United States Patent [19]

Bridgham et al.

[11] Patent Number: 4,668,476
[45] Date of Patent: May 26, 1987

[54] AUTOMATED POLYPEPTIDE SYNTHESIS APPARATUS

[75] Inventors: John Bridgham, Palo Alto; Timothy G. Geiser, La Honda; Michael W. Hunkapiller, San Carlos; Stephen B. H. Kent, Pasadena; Mark P. Marriott, Los Altos; Paul O. Ramstad, Oakland; Eric S. Nordman, San Bruno, all of Calif.

[73] Assignee: Applied Biosystems, Inc., Foster City, Calif.

[21] Appl. No.: 592,638

[22] Filed: Mar. 23, 1984

[51] Int. Cl.⁴ .............................................. C07K 1/08
[52] U.S. Cl. ..................................... 422/62; 422/107; 422/109; 422/111; 422/116; 422/134; 422/138; 364/500; 935/88; 435/289; 435/290; 435/317
[58] Field of Search ................. 422/62, 107, 109, 110, 422/111, 116, 129, 134, 138; 260/112 R; 435/69, 71, 289, 290, 317; 536/27; 364/500; 935/88

[56] References Cited

U.S. PATENT DOCUMENTS

| | | |
|---|---|---|
| 3,244,485 | 4/1966 | Coggeshall . |
| 3,356,763 | 12/1967 | Dollinger et al. ................. 422/134 |
| 3,513,145 | 5/1970 | Crawford ............................ 422/134 |
| 3,531,258 | 9/1970 | Merrifield et al. ..................... 23/252 |
| 3,557,077 | 9/1967 | Brunfeldt et al. ................. 260/112.5 |
| 3,645,698 | 2/1972 | Holybee et al. ................... 23/253 R |
| 3,647,390 | 3/1972 | Kubodera et al. ................ 23/252 R |
| 3,715,190 | 2/1973 | Park et al. .......................... 23/252 R |
| 3,846,399 | 11/1974 | Hirschmann et al. ........... 260/112.5 |
| 3,944,538 | 3/1976 | Bodanszky ................... 260/112.5 R |
| 3,951,741 | 4/1976 | Pfaender et al. ...................... 195/29 |
| 4,008,048 | 1/1977 | Hellemans et al. . |
| 4,008,736 | 2/1977 | Wittmann-Liebold et al. .... 137/606 |
| 4,065,412 | 12/1977 | Dreyer . |
| 4,192,798 | 3/1980 | Verlander et al. ........... 260/112.5 R |
| 4,285,858 | 8/1981 | Cort et al. ................... 260/112.5 R |
| 4,353,989 | 10/1982 | Bender et al. . |
| 4,362,699 | 12/1982 | Verlander et al. ................... 422/131 |
| 4,458,066 | 7/1984 | Caruthers et al. ..................... 536/27 |
| 4,483,964 | 11/1984 | Urdea et al. ......................... 422/116 |
| 4,492,787 | 1/1985 | Takashima et al. . |

FOREIGN PATENT DOCUMENTS

| | | |
|---|---|---|
| 0040099 | 11/1981 | European Pat. Off. . |
| 0042792 | 12/1981 | European Pat. Off. . |
| 0097994 | 1/1984 | European Pat. Off. . |
| 194896 | 11/1983 | Japan ..................................... 935/88 |
| 2084899 | 4/1982 | United Kingdom . |

OTHER PUBLICATIONS

T. Christensen et al., Res. Disc., vol. 214, pp. 34-35, #21407, 1982.
*Solid Phase Peptide Synthesis*, by John Morrow Stewart and Janis Dallaha Young, W. H. Freeman & Co., S. F.
"Solvation of the Polymer Matrix, Source of Truncated and Deletion Sequences in Solid Phase Synthesis", by William S. Hancock et al., J. Org. Chem., vol. 38, (Nov. 4, 1973).
"Peptide Synthesis, Part 1, Preparation and Use of Polar Supports based on Poly(dimethylacrylamide)", by Reza Arshady et al., J. Chem. Soc., Perkin Trans 1, 1981.
"Synthesis of Peptides: Method", by S. Meister and S. B. H. Kent, Proc. Eighth Amer. Pept. Sym., (1983), pp. 103-106.
"Automated Synthesis of Peptides", by R. B. Merrifield, Science, vol. 150, Oct. 8, 1965.

*Primary Examiner*—David L. Lacey
*Attorney, Agent, or Firm*—Joseph H. Smith

[57] ABSTRACT

An apparatus is provided for automatically constructing a polypeptide of high purity, up to 50 amino acids in length, using only single couplings. The apparatus includes an activation system for receiving protected amino acids, one kind at a time, having a common vessel (an activator vessel) in which to activate each of the amino acids. Also included is a reaction vessel for containing a resin used in solid-phase peptide synthesis for attaching a peptide chain thereto. A transfer system is also provided, which operates under control of a computer, to transfer the activated species from the activation system to the reaction vessel and to transfer amino acids, reagents, gases, and solvents from one part of the apparatus to another.

28 Claims, 27 Drawing Figures

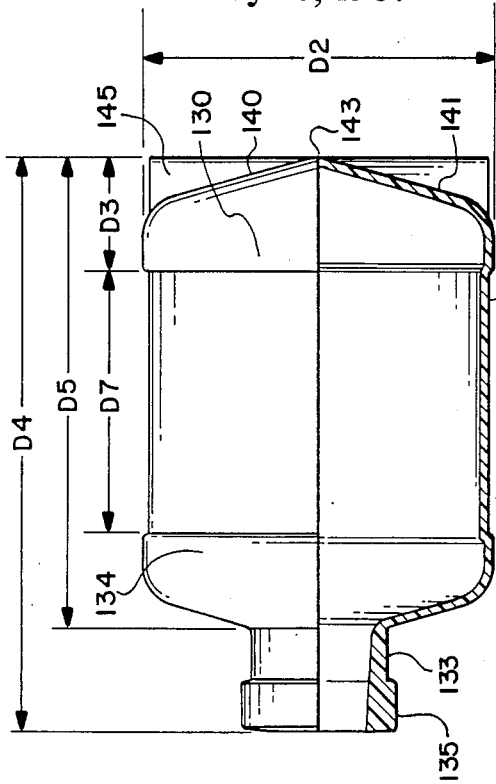
FIG. 5b
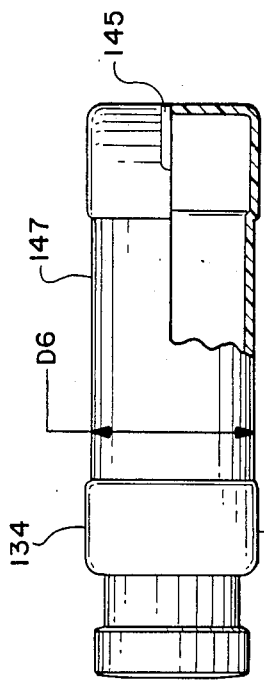
FIG. 5c
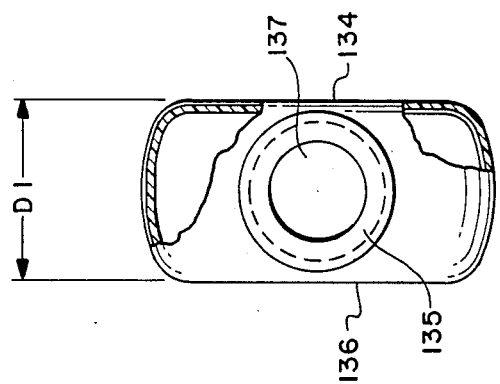
FIG. 5a
TABLE (CONTAINER DIMENSIONS)
D1  0.560 in.
D2  1.120 in.
D3  0.350 in.
D4  1.80 in.
D5  1.475 in.
D6  0.530 in.
D7  0.830 in.
FIG. 6

```
RUN FILE EDITOR.        STATIC RUN FILE NAMED XXXXXXX
    AMINO    ACTIVATOR      CONCENTRATOR    TEMP    REACTION
    ACID                                            VESSEL
     Ala     XXXXXXX        XXXXXXX         10c     XXXXXXX
     Arg     XXXXXXX        XXXXXXX         15c     XXXXXXX
     Asn     XXXXXXX        XXXXXXX         25c     XXXXXXX
     Asp     XXXXXXX        XXXXXXX         30c     XXXXXXX
     Cys     XXXXXXX        XXXXXXX         OFF     XXXXXXX
     Gln     XXXXXXX        XXXXXXX         OFF     XXXXXXX
     Glu     XXXXXXX        XXXXXXX         OFF     XXXXXXX
     Gly     XXXXXXX        XXXXXXX         OFF     XXXXXXX
     His     XXXXXXX        XXXXXXX         OFF     XXXXXXX
     Ile     XXXXXXX        XXXXXXX         OFF     XXXXXXX
     Leu     XXXXXXX        XXXXXXX         OFF     XXXXXXX
     Lys     XXXXXXX        XXXXX.XX        OFF     XXXXXXX
     Met     XXXXXXX        XXXXXXX         OFF     XXXXXXX

[CURSOR] [CURSOR] [CHANGE] [NEXT ] [STORE] [PRINT] [PREVIOUS]
 [ UP   ] [ DOWN ] [ CYCLE] [TEMP ]                 [ MENU   ]
```

FIG. 12

```
FUNCTION EDITOR         ACTIVATOR

[FUNCTION]  17                              [7] [8] [9]
[ NUMBER ]

[FUNCTION]  0  ON/OFF                       [4] [5] [6]
[  TYPE  ]

[ ACTIVE ]  17,42,61                        [1] [2] [3]
[SWITCHES]

[FUNCTION]: DCC TO ACTIVATOR                [BCK] [0] [ , ]
[  NAME  ]                                  [SPC]

ERROR: INVALID VALVE NO.
[NEXT    ] [CURSOR]                  [ENTER         ]
[FUNCTION] [RIGHT ]

[PREVIOUS] [CURSOR] [CLEAR] [PRINT] [PREVIOUS] [MAIN]
[FUNCTION] [ LEFT ] [ENTRY] [FN'S ] [ MENU   ] [MENU]
```

FIG. 13

```
REACTION VESSEL MONITOR                          VESSEL A
                                              ROM FILE IS XXXXX
   QUESTION FIELD

┌──────────────┐              ┌──────────────┐
       │  RESPONSE 1  │              │  RESPONSE 2  │
       └──────────────┘              └──────────────┘

┌───┐                                          ┌───┐
       │-->│  Ala - Asp                               │<--│
       └───┘                                          └───┘

STATUS:
        PEPTIDE NAME:
          START TIME:
            END TIME:
         CURRENT AA# :

┌───────┐ ┌────────┐              ┌───────┐ ┌─────┐
  │NEXT   │ │PREVIOUS│              │CYCLE  │ │MAIN │
  │VESSEL │ │VESSEL  │              │MONITOR│ │MENU │
  └───────┘ └────────┘              └───────┘ └─────┘
```

FIG. 14

```
RUN FILE EDITOR.         DYNAMIC RUN FILE FOR SEQUENCE XXXXXXXX

AMINO    ┌───────────┐  ┌─────────────┐ ┌────┐ ┌──────────┐
       ACID     │ ACTIVATOR │  │ CONCENTRATOR│ │TEMP│ │ REACTION │
                └───────────┘  └─────────────┘ │    │ │  VESSEL  │
   1   Ile       XXXXXXX          XXXXXXX       OFF    XXXXXXX
   2   Gly       XXXXXXX          XXXXXXX       15c    XXXXXXX
   3   His       XXXXXXX          XXXXXXX       25c    XXXXXXX
   4   Ala       XXXXXXX          XXXXXXX       25c    XXXXXXX
   5   Tyr       XXXXXXX          XXXXXXX       30c    XXXXXXX
   6   Pro       XXXXXXX          XXXXXXX       OFF    XXXXXXX
   7   Cys       XXXXXXX          XXXXXXX       OFF    XXXXXXX
   8   SP1       XXXXXXX          XXXXXXX       OFF    XXXXXXX
   9   Val       XXXXXXX          XXXXXXX       OFF    XXXXXXX
  10   Met       XXXXXXX          XXXXXXX       OFF    XXXXXXX
  11   Ala       XXXXXXX          XXXXXXX       OFF    XXXXXXX
  12   Arg       XXXXXXX          XXXXXXX       OFF    XXXXXXX
  13   Glu       XXXXXXX          XXXXXXX       OFF    XXXXXXX

┌──────┐┌──────┐┌──────┐┌─────┐┌─────┐   ┌─────┐┌────────┐
 │CURSOR││CURSOR││CHANGE││NEXT │|     │   │PRINT││PREVIOUS│
 │UP    ││DOWN  ││CYCLE ││TEMP │|     │   │     ││MENU    │
 └──────┘└──────┘└──────┘└─────┘└─────┘   └─────┘└────────┘
```

FIG. 15

```
CYCLE MONITOR                                          RUN FILE IS XXXXXXX
       RXN VESSEL              CONCENTRATOR              · ACTIVATOR
AA#: XXX OF XXX   Ala    AA#: XXX OF XXX   Ala    AA#: XXX OF XXX   Ala
CYCLE NAME: XXXXXXXX     CYCLE NAME: XXXXXXXX     CYCLE NAME: XXXXXXXX
STEP: XXX OF XXX         STEP: XXX OF XXX         STEP: XXX OF XXX
FUNCTION: #17            FUNCTION: #18            FUNCTION: #12
XXXXXXXXXXXXXXXXXXX      XXXXXXXXXXXXXXXXXXX      XXXXXXXXXXXXXXXXXXX
TIME: XXX OF XXX         TIME: XXX OF XXX         TIME: XXX OF XXX
SENSOR STATUS: gas       SENSOR STATUS: liq       SENSOR STATUS: liq ┌───────────┐           ┌────────────────┐          ┌──────┐
   │ INTERRUPT │           │ REACTION VESSEL│          │ MAIN │
   │  STATUS   │           │    MONITOR     │          │ MENU │
   └───────────┘           └────────────────┘          └──────┘
```

CYCLE COMPILER - DEFINITIONS

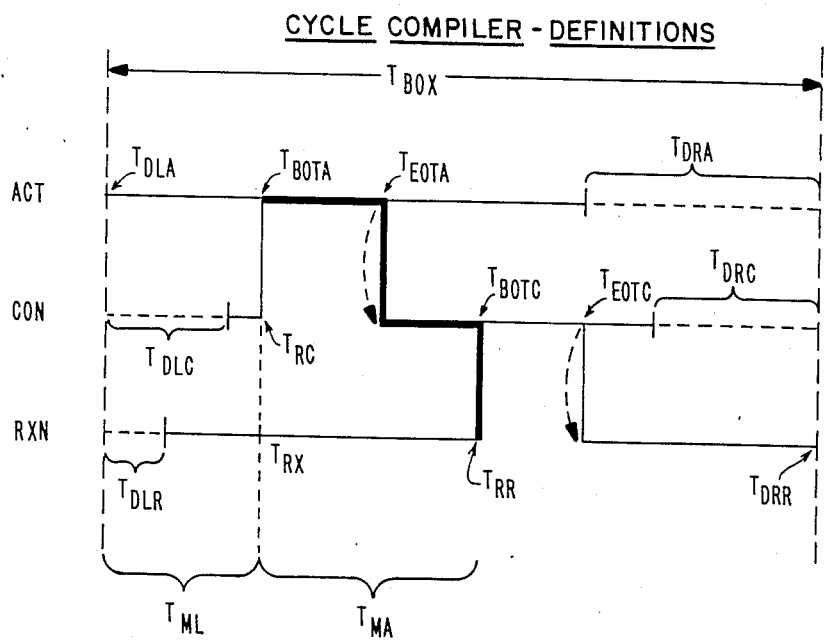

A = Activator Vessel
C = Concentrator Vessel
R = Reactor Vessel

| | |
|---|---|
| $T_{DLA}$, $T_{DLC}$, $T_{DLR}$ | Left side delay time for A, C, R |
| $T_{BOTA}$, $T_{BOTC}$ | Begin transfer time for A, C |
| $T_{EOTA}$, $T_{EOTC}$ | End of transfer for A, C |
| $T_{DRA}$, $T_{DRC}$, $T_{DRR}$ | Right side delays for A, C, R |
| $T_{RC}$, $T_{RR}$ | Ready to receive times for C, R |
| $T_{BOX}$ | "Rectangular" time defined by left side max and right side max |
| $T_{ML}$ | Left side max (maximum of components of cycles to left of $T_{BOTA}/T_{RC}$ Arm) |
| $T_{MA}$ | Major Arm Time (outlined in black) |
| $T_{AT}$, $T_{CT}$, $T_{RT}$ | Total time for each cycle |

FIG. 20b  TABLE

| ANALYTICAL METHOD | STEP YIELD (%) | | | | | | | | | |
|---|---|---|---|---|---|---|---|---|---|---|
| QUANTITATIVE NINHYDRIN MONITORING ① | — | 99.9 | 99.6 | 99.5 | 99.4 | 99.1 | 99.2 | 99.2 | 99.1 | 98.9 |
| PREVIEW QUANTITATION BY SOLID PHASE SEQUENCING OF PROTECTED, RESIN BOUND PEPTIDE ① | — | — | 99.4 | — | 99.3 | 99.1 | 99.2 | — | 98.9 | 98.7 |
| AMINO ACID RESIDUE | GLY← | ASN← | ILE← | TYR← | ASP← | ILE← | ALA← | ALA← | GLN← | VAL |

AUTOMATED POLYPEPTIDE SYNTHESIS APPARATUS

FIELD OF INVENTION

This invention relates to apparatus for the automated synthesis of polypeptides, and particularly to apparatus for automatically pre-forming activated species of (alpha-amino protected) amino acids immediately prior to introduction into solid phase synthesis reactions.

BACKGROUND TO THE INVENTION

Since its inception in 1962, R. B. Merrifield's concept of solid phase peptide synthesis has seen many improvements and has now become an established technique in the art. Literally hundreds of investigations have been published describing the chemical details of the method (See for example, Merrifield, R. B.: Science 150, 178 (1965); Merrifield, R. B.: Sci. Amer. 218, 56 (1968); Stewart, J. M., Young, J. D.: In: Solid Phase Peptide Synthesis. San Francisco, Calif.: Freeman 1969; and Erickson, B. W., Merrifield, R. B.: In: The Proteins (eds. Neurath, R. L. Hill), III. Ed., Vol. 2, pp 255-527. New York: Academic Press 1976).)

Typically, solid phase peptide synthesis begins with the covalent attachment of the carboxyl end of an (alpha-amino protected) first amino acid in the peptide sequence through an organic linker to an insoluble resin bead (typically 25–300 microns in diameter), illustrated by:

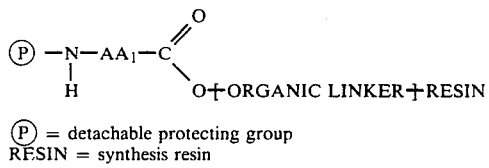

$\text{P}$ = detachable protecting group
RESIN = synthesis resin

A general cycle of synthesis then consists of deprotection of the resin bound alpha-amino group, washing (and neutralization if necessary), followed by reaction with with some carboxyl activated form of the next (alpha-amino protected) amino acid acid to yield:

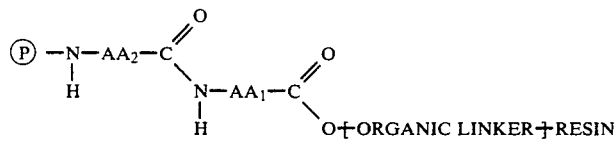

Repetition of the cycle to the $n^{th}$ amino acid then yields:

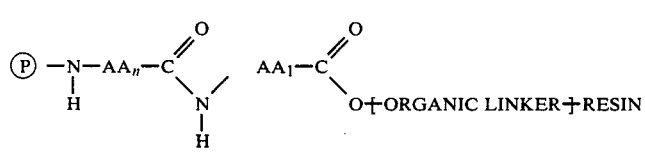

At the end of the synthesis, the link of the peptide to its polymer support is cleaved, and the dissolved peptide is separated from the insoluble resin and purified.

Although this process is simple in principle, in practice it can be quite difficult to obtain peptides over about 30 amino acids long which have any substantial purity. The reason for this is that the average step yield has a profound effect on the purity of the product peptide, as illustrated by the values in the following table for synthesis of a 30 amino acid peptide.

TABLE

| 30 AMINO ACID PEPTIDE | |
|---|---|
| Average Step Yield (%) | Product Purity (%) |
| 95.0 | 21 |
| 99.5 | 86 |
| 99.7 | 91 |

The results are even more problematic for longer peptides, eg. for a target peptide with 101 residues, a step yield of 99.0% provides a product of only 36% purity. In all cases, the by-products of peptide synthesis consist of a complex mixture of molecules which are chemically similar to the target peptide. Chromatographic purification can be extraordinarily difficult and time consuming as the relative amount of by-product molecules begins to exceed about 25%.

The efficiency of step yield is dependent on many factors such as the nature and quality of the protected amino acids, solvent purity, chemical integrity of the resin, the chemical nature of the organic linker, the form of the activated carboxyl of the amino acid, efficiency of the wash step, the synthesis protocol, and in some instances the identity of an amino acid in conjunction with a particular sequence segment to which it is being added.

Each of the above factors, when not optimally controlled, will contribute some significant increment to yield reduction in every coupling step. At the present time, the complexity of these factors is such that average step yields in solid phase peptide synthesis are typically in the range of 93–97% for both manual and automated executions. For practical applications on a commercially reasonable scale, such as for the development of pharmaceuticals, enzyme substrates and inhibitors, hormones, vaccines, and diagnostic reagents, such low step yields significantly increase costs of production and in many cases make such direct solid phase synthesis of peptides impractical.

Prior art peptide synthesizers operate essentially as "washing machines" which automate the monotonous fluid manipulations of deprotection, addition of coupling agent, and washing. In no case do existing commercial peptide synthesizers form an activated amino acid species outside or independent of the reaction vessel. Typically, protected amino acid and DCC are added to the reaction vessel containing the resin bound, incipient peptide chain so that activation of the amino acid occurs in the presence of the deprotected alpha-amino group. This approach both limits the possibility (or feasibility) of optimizing activation conditions for individual amino acids and requires that any modification of activation conditions be done in the presence of the deprotected alpha-amino group and the growing, resin-bound peptide chain. This fact makes it difficult, if not impossible, to optimize activation parameters by analyzing rates of formation and relative thermal and solvent stabilities of the individual, activated amino acid species. Additionally, the ability to use various thermal inputs during the activation process can only be done in the presence of the peptide chain.

SUMMARY OF THE INVENTION

In accordance with the preferred embodiment of the invention, an apparatus is provided for automatically constructing a polypeptide of high purity, up to 50 amino acids in length, using only single couplings. The apparatus includes an activation system for receiving protected amino acids, one kind at a time, having a common vessel (an activator vessel) in which to activate each of the amino acids in the order received to form a sequence of aliquots of activated species of each of the amino acids, each aliquot containing one kind of amino acid and the sequence of aliquots of each kind of amino acid being in the order desired in the peptide. Also included is a reaction vessel for containing a resin used in solid-phase peptide synthesis for attaching a peptide chain thereto. A transfer system is also provided, which operates under control of a computer, to transfer the activated species from the activation system to the reaction vessel and to transfer amino acids, reagents, gases, and solvents from one part of the apparauts to another. The activator system also includes a temperature controlled concentrator vessel in which an activator solvent, which is used in the activator vessel when creating the activated species of the amino acid, is replaced by a coupling solvent to enhance the coupling of the activated species to the peptide chain in the reaction vessel. This replacement is accomplished a short period of time (typically less than thirty minutes) before the activated amino acid is introduced into the reaction vessel, by adding the coupling solvent to the concentrator vessel together with the activated species and the activator solvent, and sparging gas through the resulting solution to selectively evaporate the activator solvent. The activator solvent is chosen with a boiling point lower than the boiling point of the coupling solvent. The concentrator is heated as necessary to replace heat lost by evaporation.

Also included in the synthesizer system is a vortexer for affecting total washing of materials in the reaction vessel and the reaction vessel itself, an automated peptide resin sampling system, and an autodelivery system for providing individual containers of amino acid to the synthesizer in the order desired in the peptide sequence. Also, a specialized container for use in the autodelivery system is provided which has a vee-shaped bottom in order to permit extraction of as much amino acid as is practicable which permits precise control over stoichiometry. A liquid sensor system is also included to monitor transitions between gases and liquids in specific tubes in the synthesizer in order to provide input signals to the computer system for control purposes.

The computer system software which controls the operation of the synthesizer is organized according to a series of menus which allows the user of the system to select individual cycles of operation for each vessel in the synthesizer. In addition each cycle can be user-defined into a series of functions, each of which corresponds to a standard set of instructions for individual valves and other switched systems associated with the synthesizer. Also, using the menu system, the user can define alternative individual functions as well.

In addition to the menu driven control system, an algorithm has been developed which is related to the organization of the computer software into individual cycles for each vessel. Operating the synthesizer according to the algorithm provides for optimum efficiency in the production of a peptide for any given selection of cycles.

BRIEF DESCRIPTION OF THE DRAWINGS

FIGS. 5a, 5b, and 5c are three views of a container used in the autodelivery system.

FIG. 6 is a table showing the dimensions of the container used in the autodelivery system.

FIGS. 8-16 illustrate various menus used in the computer system to define operations for running the synthesizer apparatus.

FIG. 18 is a diagrm to provide definitions for use in the calculational scheme for optimizing production of peptide.

DETAILED DESCRIPTION OF THE INVENTION

Figure 1A:
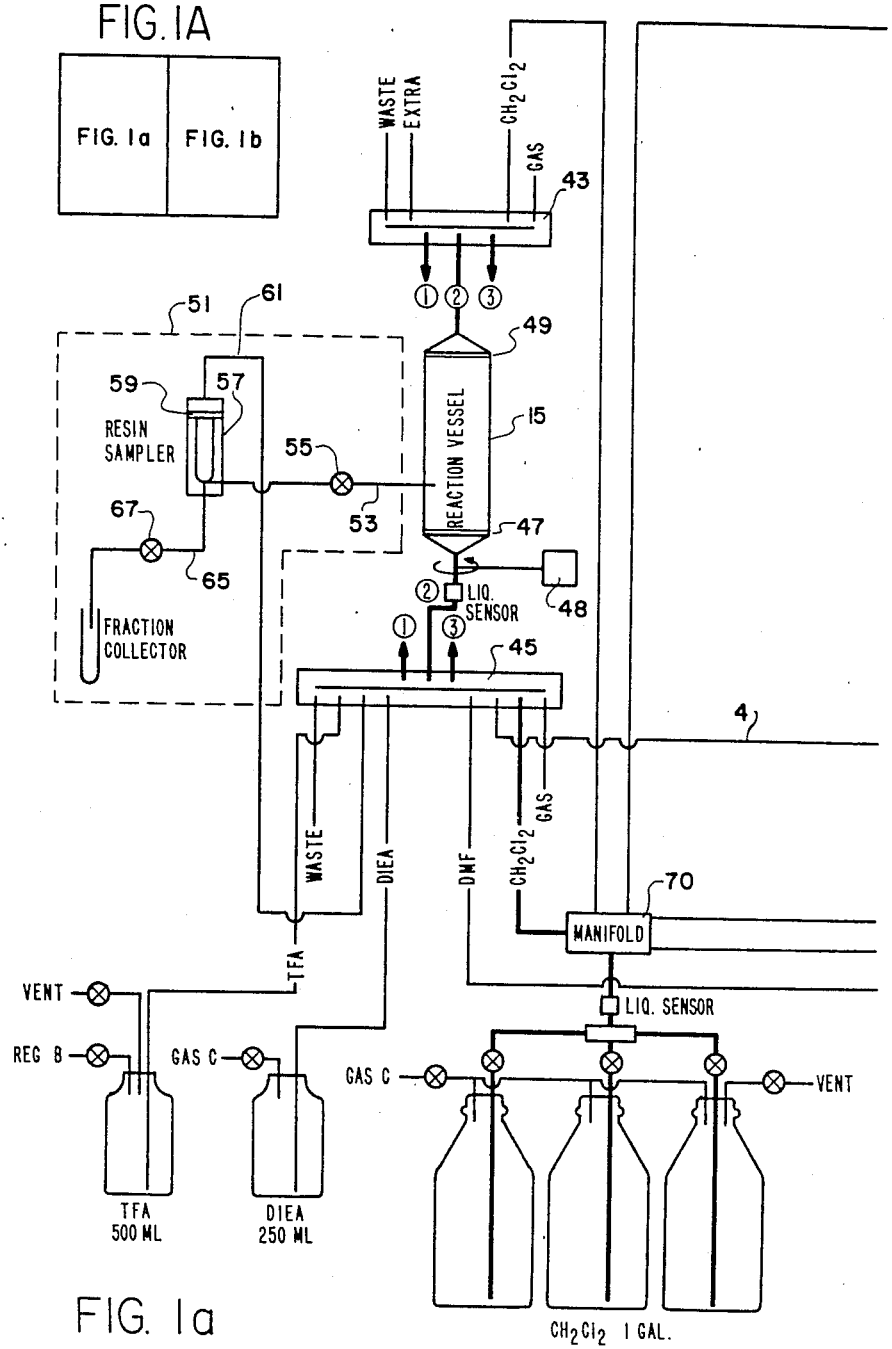
FIGS. 1a and 1b illustrate the fluid delivery system of the apparatus according to the invention.

Before the details of the apparatus of the invention are described, it is useful first to understand the chemical approach of the solid phase peptide synthesis which the apparatus is designed to optimize.

For the present invention, the preferred mode of the synthesis takes place primarily in three phases. The first, or activation phase involves the production of the (alpha-amino protected) amino acid symmetric anhydride as the acylating species:

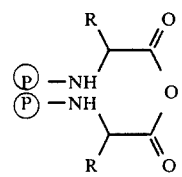

Symmetric anhydrides are extremely effective, activated carboxyl forms of amino acids, since their couplings are substantially free of racemization in the absence of base and since quantitative single couplings are usually assured for most amino acid additions, with the exception of asparagine, glutamine, and arginine—each of which is more efficiently coupled by an alternative activation method which will be discussed later. The generally quantitative nature of couplings with symmetric anhydrides makes them most useful where automated synthesis precludes convenient step by step quantitative monitoring. The apparatus herein described automatically synthesizes symmetric anhydrides immediately before incorporation into the peptide chain. Because of the marginal stability of symmetric anhydrides and their difficulty of isolation in pure form, their use in the past has been limited to manual preformation followed by introduction into an automated synthesis machine.

The procedure for synthesizing pre-formed symmetric anhydrides (PSA's) consists of reacting 0.5 equivalents of dicyclohexylcarbodiimide (DCC) with 1.0 equivalent of protected amino acid in dichloromethane (DCM) according to the equation:

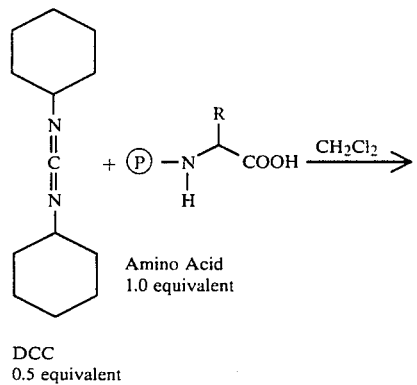

DCC
0.5 equivalent

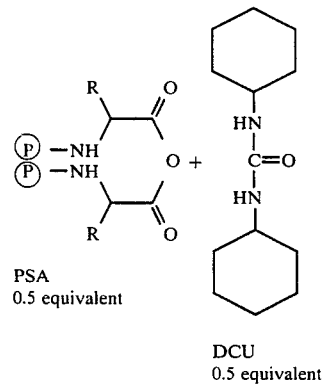

PSA
0.5 equivalent

DCU
0.5 equivalent dichloromethane being an optimal solvent for the synthesis of PSA's, particularly where the alpha-amino protecting group P is the t-butyloxycarbonyl group (t-BOC). The DCU, formed in the reaction, however, is very insoluble in dichloromethane and precipitates during the PSA reaction. After completion of the reaction, the PSA/DCM solution is filtered away from the DCU precipitate, and the second, or concentration phase is begun. In the concentration phase the DCM is removed and replaced by polar aprotic solvent, preferably N,N-dimethylformamide (DMF), to enhance coupling efficiency during later solid phase reactions. The third, or reaction phase then follows the general schema described in the Background of the Invention whereby to attach an additional amino acid to the sequence the carboxyl end of the PSA is reacted with an alpha-amino deprotected resin-bound peptide chain.

APPARATUS

In accordance with the preferred embodiment of the invention, an apparatus for achieving the synthesis described above is illustrated in FIGS. 1A, 1B, 2 and 3, which show respectively a fluid delivery system, for routing the various amino acids, reagents, solvents and gases throughout the apparatus; a computer system for effecting automatic control over the numerous switches which control the valves, sensors, temperature of certain vessels, and motors in the apparatus; and an autodelivery system for transporting protected amino acids to the apparatus in the order desired in the peptide sequence.

The fluid delivery system includes two systems made up of three primary vessels: an activation system 10 having an activator vessel 11, where the PSA is formed, and a concentrator vessel 13, where the PSA/DCM solution from the activator vessel is transferred so that DCM may be replaced by DMF to enchance coupling; and a reaction system having a reaction vessel 15 which contains the growing resin-bound peptide chain.

Activator vessel 11 is typically cylindrical, about 40 ml in volume, and is preferably constructed of glass in order for the operator of the device to visually inspect the progress of reactioons or cleaning cycles. At the bottom of the activator vessel is a glass frit 17 of coarse pore size which is used to filter the DCU precipitated from the PSA/DCM solution when transferring the solution to the concentrator vessel 13. Activator vessel 11 also contains an overhead nozzle 19 which faces upward in order to achieve a total washdown of the headspace and walls after each amino acid is transferred out of the vessel. Activator 11 is coupled to the autodelivery system and to various gases and reagents as shown via a valve block 23, which is an assembly of zero dead volume valves such as that described in U.S. Pat. No. 4,008,736, issued Feb. 22, 1977, entitled VALVE ARRANGEMENT FOR DISTRIBUTING FLUIDS, by Wittman-Liebold, et al., as are all other valve blocks in the system. Valve block 23 is operated under the control of the computer system, as are all other valve blocks and gas valves in the apparatus. Activator 11 is coupled via nozzle 19 to another valve block 25 which controls the flow of methanol and DCM into the vessel for dissolving DCU precipitate for cleaning and which controls the pressure inside the vessel to effect transfers of materials into and out of the vessel from block valve 23. Transfers from the bottom of the vessel take place through a translucent tube 29, typically constructed of Teflon TM, the transfers being monitored by the computer system by means of a liquid sensor 27 which detects transitions in tube 29 between gases and liquids. Typically tube 29, and other tubes in the system to which similar liquid sensors are attached have a roughly calibrated flow resistance and operate at a fixed known pressure during transfers, so that the length of time required for a transfer corresponds directly to the volume of material which is transfered. For DCC and HOBT, which require specific volumes, a calibrated delivery loop is used to achieve a higher accuracy. Hence, the computer system can accurately monitor all flow into and out of the activator vessel. Although details of the liquid sensor will be described later, it is important to emphasize that the use of liquid sensors is not required for operation of the apparatus.

They are useful however in achieving better system control.

The next major section of the fluid delivery system is the concentrator vessel 13. Its construction is substantially the same as that of activator vessel 11, and includes an overhead nozzle 31, and a glass filter frit 35 at the bottom. In addition, however, the concentrator vessel also has a band heater 37 attached thereto, which is used to control the temperatures inside the vessel through the use of a thermistor as the DCM in the PSA/DCM solution is replaced by DMF. Attached to concentrator vessel 13 is a valve block 33, and a translucent transfer tube 29 monitored by a liquid sensor 40. Transfers through tube 39 are controlled by the computer system by means of valve block 41.

Figure 4:
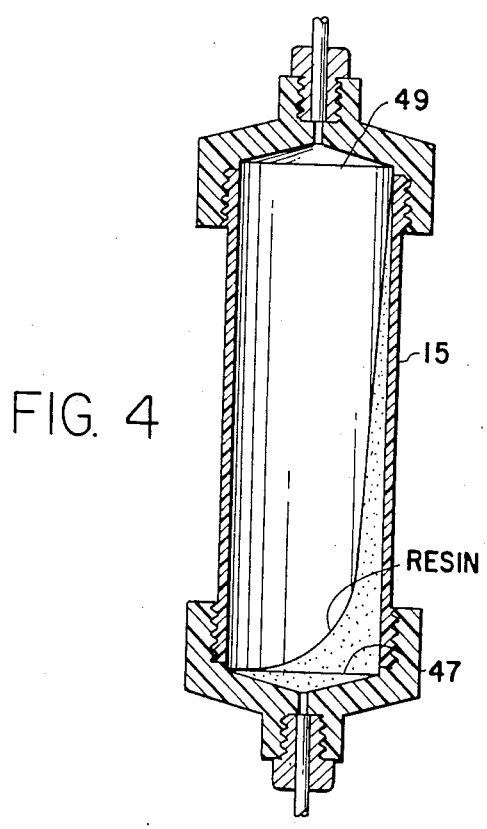
FIG. 4 is a cross-sectional view of a reaction vessel according to the invention showing the results of vortexing of fluids contained therein.

The next major section of the fluid delivery system is the reaction vessel 15, which in the preferred embodiment is a right circular cylinder oriented vertically and is constructed of a machined fluorocarbon polymer, such as Teflon TM or KEL-F TM. The vessel is valved at the top by a valve block 43 and at the bottom by a valve block 45, each valve block being isolated by a filter such as membrane 47 and membrane 49 which are typically constructed of a material such as ZITEX TM, produced by Chemplast Inc. of Wayne, N.J., although glass frits could also be used. The reaction vessel is designed to be opened conveniently, both for initial charging with the loaded resin and for periodic removal of sample aliquots. As illustrated in FIG. 4, this is accomplished by threading the top and bottom of the reaction vessel cylinder to accommodate threaded caps. The threaded caps are also used to hold the membranes in place, and each cap is configured to accept a tube in order to transfer fluids into and out of the reaction vessel. A typical volume for the reaction vessel can vary widely, depending on the length of the peptide chain to be synthesized and the weight and amino acid loading of the synthesis resin. For example, for chains up to 50 amino acid units in length, starting with 0.5 grams of resin (0.5 m mole of amino acid), a preferred size is about 40 ml. Those skilled in the art of solid phase synthesis will realize that the resin may swell from three to five fold due to solvent imbibement during synthesis. Mass increase as a result of growth of the peptide chain can cause an increase in the occupied volume of the reaction vessel from 10% initially to as much as 80% at the end of the synthesis, depending on the length of the peptide.

In order to promote efficient coupling and to avoid agglomeration of the resin beads it is important to agitate the reaction vessel at various stages in the reaction cycle. Also, it is especially important that the entire inner surface of reaction vessel 15 be completely rinsed during each wash cycle between the additions of PSA's from the concentrator vessel. To achieve this agitation, the bottom of the reaction vessel is moved in a circle having a radius of about 0.093 in., about its center axis at about 1500 rpm, by a motor 48 (connected by a pully to an eccentric on the bottom of the reaction vessel) under control of the computer system, while the center of the top of the reaction vessel is held substantially fixed, with the vessel itself being prevented from rotating. The result is a conically rotational motion of the fluid resin mixture in the reaction vessel about the vertical axis which has the appearance of a vortex.

This "vortex" agitation mode enables use of very small volume increments of wash solvent for all washing operations, thus greatly improving the efficiency of removal of spent reagents and reagent by-products from the synthesis resin, since it is much more efficient to extract these materials by successive partitioning, than by a single extraction. The ability to use small volume increments is a result of the angular momentum of the fluid resin mixture imparted by the conical motion. This "vortexing" action creates a distribution of fluid in the vessel as depicted in FIG. 4, wherein the fluid in the reaction vessel can be made to contact all interior surfaces of the reaction vessel, for very small volume increments of the solvent by proper choice of the speed of rotation. The result is more efficient washing of the resin by smaller volumes of expensive solvents.

Additionally, this mode of agitation prevents resin agglomeration and allows total fluid-resin interaction without the use of impeller type mechanical agitation. With mechanical agitation, the shear and resin abrasion caused by the impeller can fracture the resin beads into smaller and smaller particles which can eventually clog the filters, such as membranes 47 and 49, thus forcing interruption of the synthesis process. Such an interruption can have dire effects on synthesis, e.g. restriction of flow (out of the Reaction vessel) could occur during an acid deprotection step, thereby subjecting the resin bound peptide to the degradative effects of overlong acid exposure. With the vortex agitator there are no impeller type shear or abrasive effects on the resin beads. Those skilled in the art will understand that although in the preferred embodiment the reaction vessel has been constructed in the shape of a right circular cylinder, other shapes can also be used, provided they are not antagonistic to the relatively smooth swirling of the fluid in the vessel, e.g. a shape such as that of a wine glass appears to have some desirable properties for the washing cycle. Also, for maximum efficiency, the apparatus is typically implemented with three reaction vessels 15 while using only one concentrator vessel 13 and one activator vessel 11, with the fluid distribution from these latter two vessels appropriately valved to operate with each of the three reaction vessels and their corresponding valve blocks 43 and 45. It should be understood, however, that each of these reaction vessels corresponds to a separate sequential process for creating a peptide, i.e. the first peptide is formed in the first reaction vessel, then the second peptide is formed in the second reaction vessel, then the third peptide is formed in the third vessel.

In order to monitor the progress of the synthesis in the reaction vessel, a resin sampler system 51 is provided. The sampler includes a tube 53 connected into the side of the reaction vessel for extracting materials therefrom, the flow through the tube being controlled by a computer controlled valve 55, typically a solenoid operated pinch valve. Tube 53 extends into the bottom portion of resin sampler reservoir 57 which has a membrane 59, typically ZITEX TM located at the top. Also connected to the top of reservoir 57, on the opposite side of membrane 59, is a tube 61 which is connected to valve block 45. From the bottom of the reservoir extends another tube 65, which is controlled by a valve 67 also typically a solenoid operated pinch valve (to achieve zero dead volume), for collecting fractions from the reservoir.

Figure 1B:
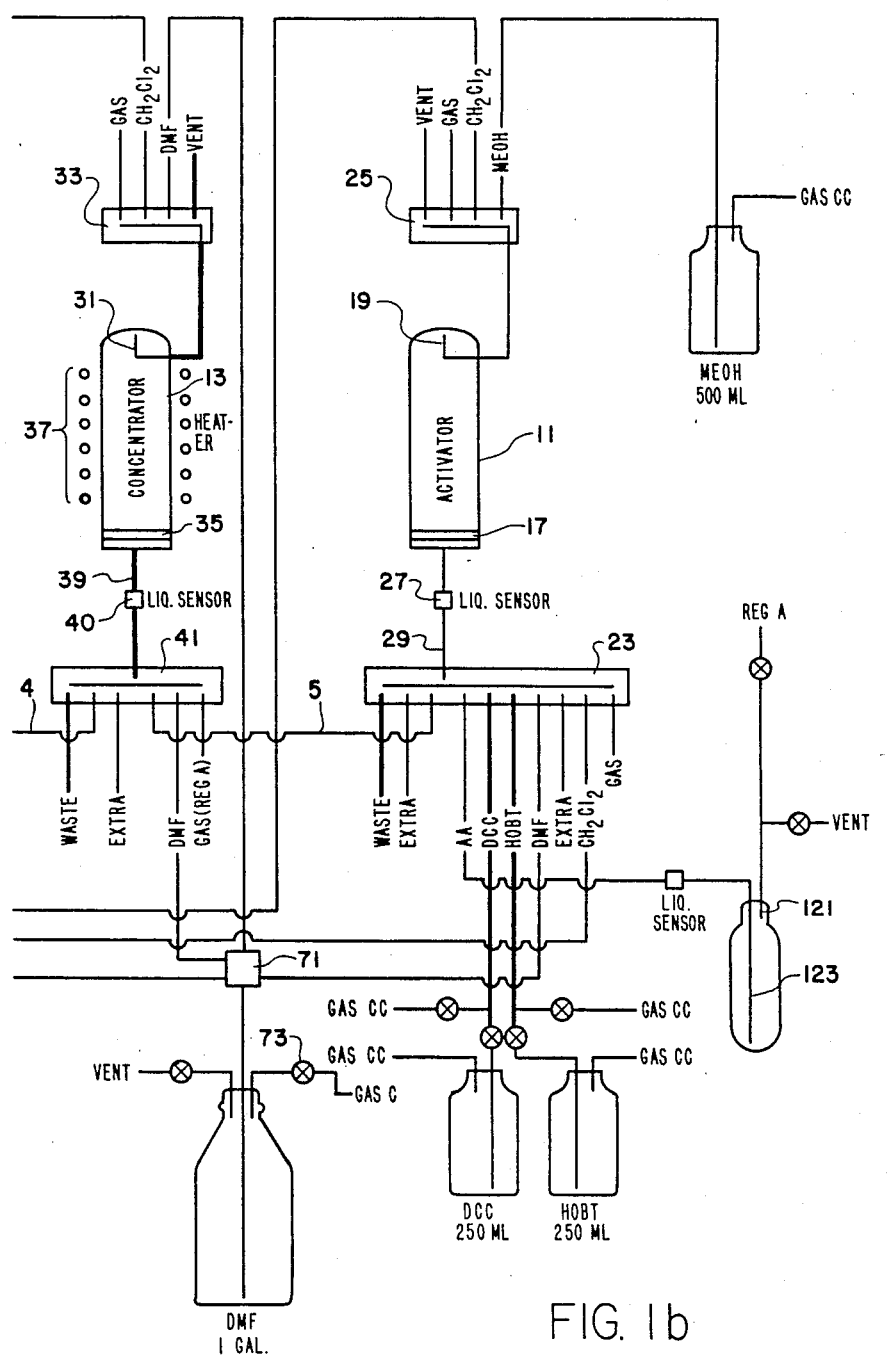

The gas distribution system for achieving the desired transfers within the apparatus is illustrated in both FIGS. 1A and 1B, and consists of three gas manifold, manifold C, manifold CC, and manifold D, and accompanying regulators for controlling the distribution from bottles and through the valve blocks. Also included are two smaller manifolds, manifold 70 for distributing DCM throughout the apparatus and manifold 71 for distributing DMF to the activator vessel and the concentrator vessel. Gas flows throughout the system are controlled by the computer system by means of solenoid operated valves such as valve 73; (e.g. such as fluorocarbon valves are made by Angar, Incorporated.) and by the valve blocks already discussed.

Figure 2:
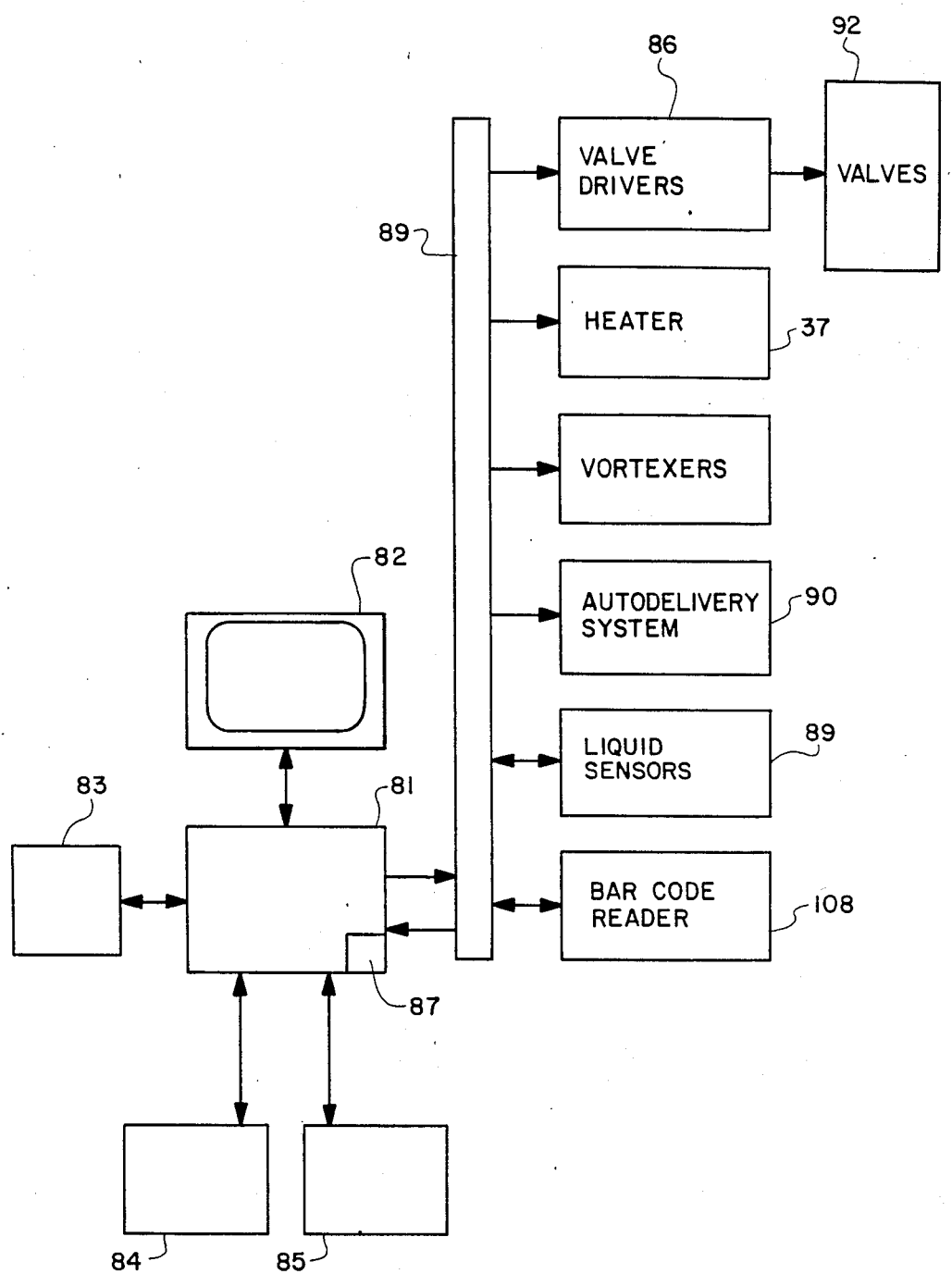
FIG. 2 illustrates the computer system used for controlling the apparatus.

FIG. 2 shows a schematic representation of the computer system which consists of a microprocessor based microcomputer 81 having an arithmetic unit 87; a mass storage device 84, such as a floppy disk; a random access memory (RAM) 83 for high speed; a hard copy output device 85, such as a printer; and a touch screen 82 which, in the preferred embodiment, operates as the only input device available directly to the user. The system operates a switching apparatus 89, a switch being the basic on/off device which the opeator uses to control all the valves, the vortexers, the autodelivery system 90, and the heater 37. Typically, there is a one-to-one correspondence between devices and switches in the system so that each device corresponds to a particular switch number. For example, switches 0–63 may refer to valve numbers 0–63; the heater may be controlled by switch 64, etc. Also to implement other elements of automatic control, the microcomputer 81 receives input signals from the liquid sensors in order to identify the times of gas-liquid and liquid-gas transitions, and it receives information from a bar code reader 108 located on the autodelivery system, for cross-checking the identification of amino acids entering the synthesizer.

Figure 3:
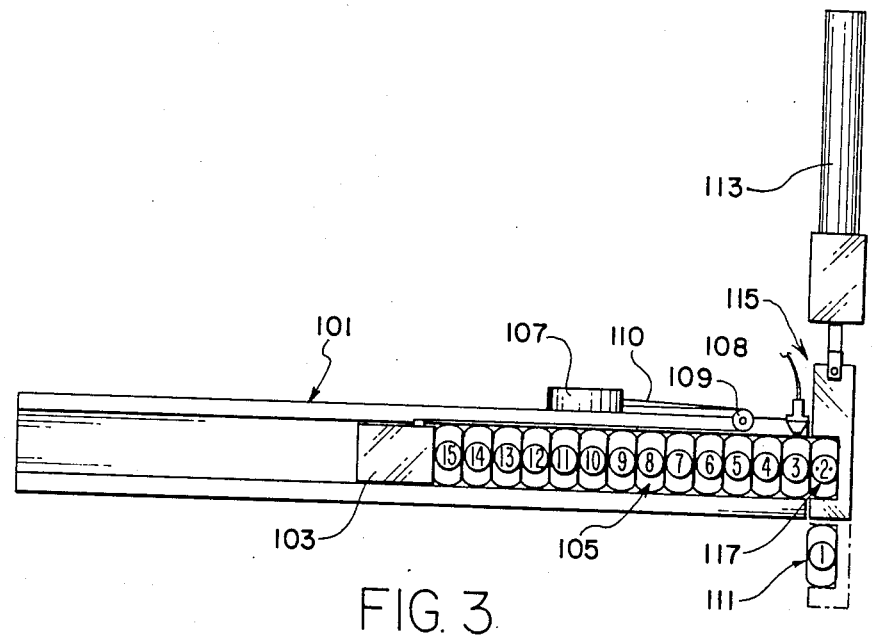
FIG. 3 is a top view of an autodelivery system for providing individual containers to the synthesis apparatus.

Shown in FIG. 3 is a top view of the autodelivery system. The system has a guideway 101 which serves as a track to hold and control the direction of motion of an array of cartridges, such as caritridge 105. Each of the cartridges in the array contains an individual protected amino acid, and is placed in the array in the sequence that is desired in the peptide to be synthesized. For convenience, the guideway is open for visual inspection of the array and is oriented to correspond to the peptide with the carboxyl terminus on the right, which mimics the typical way peptides are depicted in the literature and facilitates the comparison of the sequence in the loaded guideway with that of the desired peptide. To hold the array of cartridges, a pressure block 103 is held against the last cartridge of the array by a spring reel 107 which is typically implemented with a steel restorer tape 110 entrained over a pulley 109. This allows movement of the pressure block along the guideway while still providing a substantially constant force against the array of cartridges, thus accommodating arrays of different lengths which correspond to peptides of different lengths. Additionally, more than one peptide can be synthesized from a single array of cartridges. On the end of the guideway opposite pressure block 103 is an ejector system 115 driven by an air cylinder 113, for holding cartridges in a sampling position 117 such as that shown for cartridge number 2, and for ejecting the cartridges once the aminio acids therein are educted. Position 111 for cartridge number 1 illustrates the eject position of ejector system 115, from which the spent cartridge falls down a shoot (not shown) and is disposed of. When the ejector returns to its normal position after ejecting, the constant force spring 107, acting through pressure block 103, forces the next cartridge into delivery position.

Also included in the autodelivery system is a bar code reader 108. In the preferred embodiment, each cartridge is labeled with a bar code unique to the kind of amino acid it contains. When a cartridge progresses down the guideway to the location of the bar code reader, the readers read the bar code label and sends the information to the computer system. If the computer has been pre-set for a particular polypeptide, it performs a consistency check to ensure that the cartridge is in the correct position in the sequence for that polypeptide. If the computer has not been pre-set for a particular polypeptide, the system runs open loop and the computer uses the information from the bar code to call the synthesis protocol to be used for that particular amino acid in the cartridge and to record the amino acid used. Also, each cartridge contains a stoichiometrically correct quantity of amino acid.

In order to educt amino acid from a cartridge, the system is provided with two syringe needles (shown in FIG. 1A), a needle 121 for supplying gas pressure and for venting and a needle 123 for supplying DCM to the cartridge to dissolve the amino acid and for educting the dissolved amino acid and DCM. The two needles are typically mounted vertically and connected to an air cylinder (not shown) for moving the needles up and out of the way when a new cartridge is moved into place, and for driving the needles down through the top of cartridge for the mixing and educting operations.

FIGS. 5a, 5b, and 5c show the details of the typical cartridge 105 used in autodelivery system. In the preferred mode, the container is constructed of blown, high density, polyethylene, and has a body portion 130 of substantially rectangular cross-section capable of holding about 7 ml. It also has a neck portion 133 onto which is attached a serum-finished cap 135 having an integral septum 137, which acts to provide a positive seal of the cap to the neck. As illustrated in FIGS. 5a and 5b, the dimension D1, ($\sim$0.5 in.) is typically considerably less than dimension $D_2$ ($\sim$1.120 in.) so that a relatively large number of cartridges (up to 50) can be used in an array on guideway 101 without the length of the array becoming unwieldy. Also, to promote a proper positioning in the array, the cartridge has two substantially flat surfaces 134 and 136 on each face.

The bottom of the cartridge is formed in the shape of two planes 140 and 141 intersecting at an angle to form a vee-shaped trough. When the cartridge is in the sampling position in the autodelivery system, needle 123 descends very close to the line of intersection 143 of the two planes, which corresponds to the locus of points having the lowest elevation in the cartridge, i.e. in the bottom of the cartridge. The needle being located near the lowest point in the cartridge helps to ensure that all of the material in the cartridge is educted, thereby making possible careful control of stoichiometry. In order to stabilize the cartridge as it sits in guideway 101, a flange 145 extends across the bottom of the cartridge in a direction perpendicular to the line of intersection 143. The vee-bottomed trough and flange 145 make it possible for the cartridge to stand unassisted in a stable upright position. The cartridge also includes an indentation 147 around its circumference to promote precise placement of a bar code label to ensure the accuracy of bar code reader 108 in reading the label.

FIG. 6 is a table listing the various dimensions of the bottle.

Figure 7A:
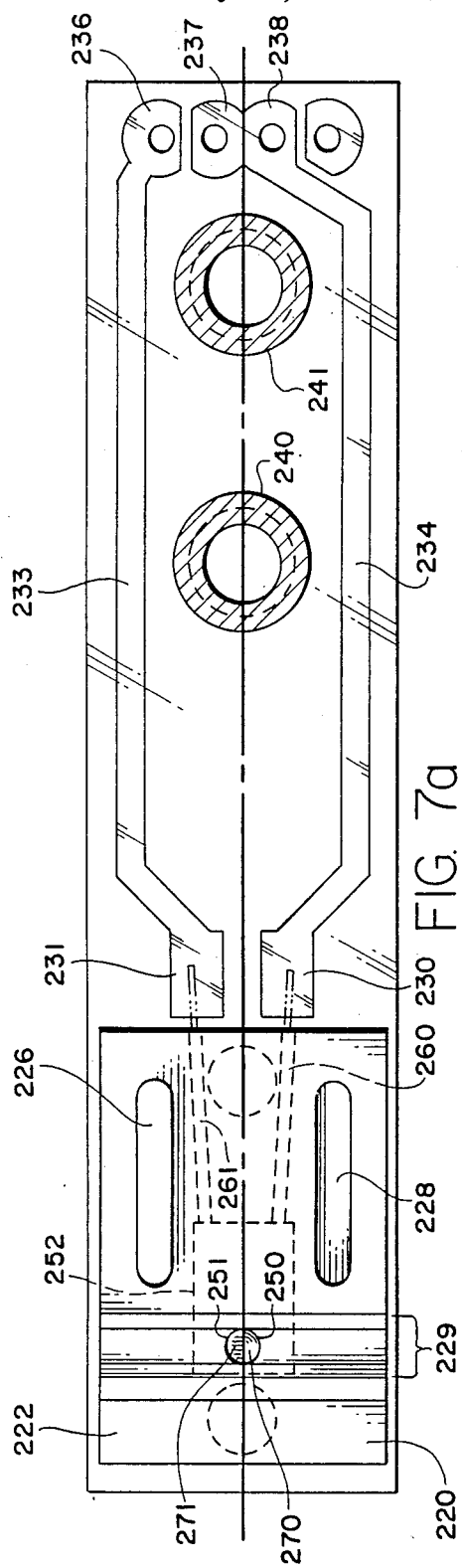
FIGS. 7a and 7b show two views of a liquid sensor used in the apparatus.
Figure 7B:
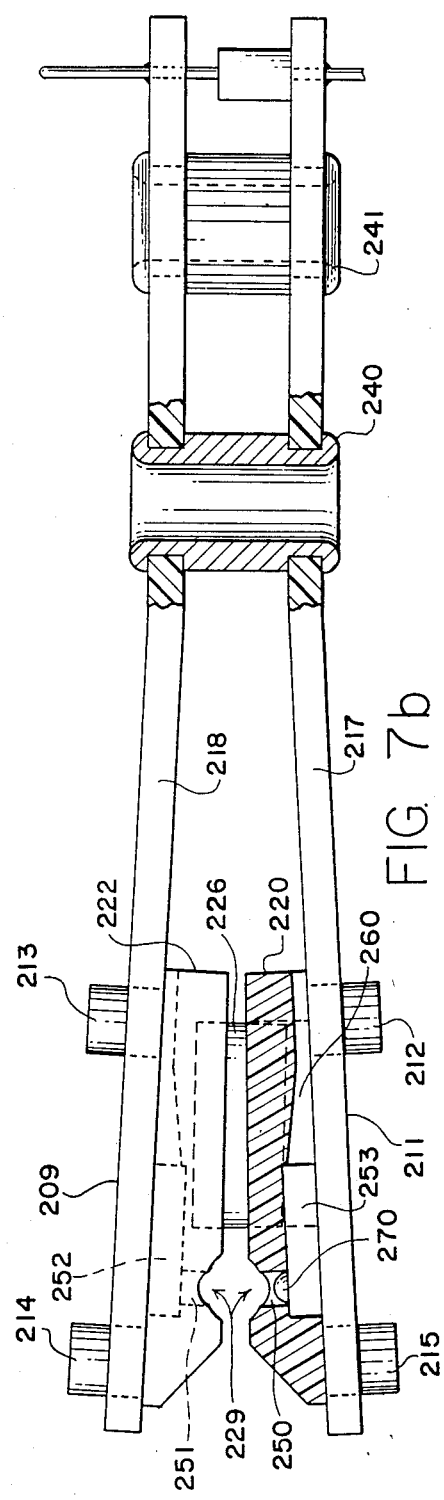

Illustrated in FIGS. 7a, and 7b are cutaway views of a typical liquid sensor used in the synthesizer. In the top view of FIG. 7b, the device is symmetric about the centerline CL, so the top half of FIG. 7b corresponds to the bottom view of the top half of the device, and the bottom half of FIG. 7b corresponds to the top view of the bottom half of the device. The device is made up of a clothespin-like tube-holder housing having a top portion 222 and a bottom portion 220, typically constructed of glass-filled nylon or plastic, each of which has a groove 229 with a double curvature extending across the width thereof to accommodate a translucent tube. The double curvature is provided to enable the top and bottom portion to positively engage two different tube diameters, which in the preferred embodiment are typically one-eighth or one-sixteenth of an inch in outside diameter and constructed of TEFLON TM. The top and bottom portions 222 and 220 are mounted by pegs 212, 213, 214, and 215, to two substrates, 209 and 211, respectively, which are typically constructed of printed circuit board material (phenolic). At the end opposite the tube-holder, the substrates are held a fixed distance apart by two rivets 240 and 241 of substantially the same length. By providing a thickness of the tube-holder housing, from top and bottom, which is thicker than the length of the rivets, the substrates provide a spring-like force to keep the top and bottom portion of the housing together, thereby firmly holding the tube in groove 229. Also to ensure accurate alignment of the top and bottom portions, a key arrangement is provided with keys 225 and 226, located on each side of the top portion which fit into holes (not shown because of the cutaway in FIG. 7b) and 228 located in bottom portion 220. In the side view of FIG. 7a, bottom portion 220 has been cut away to reveal a hole 250 in which is located a photodiode 270. Immediately opposite hole 250 across groove 229 in an identical hole 251 located in top portion 222 for accommodating a photodetector 271, which is used to detect the change in intensity of light received from the photodiode when the interface between a liquid and gas, or between a gas and liquid moves down the tube held in groove 229, the change in intensity being due to the difference in focusing of the light rays due to the difference in refractive properties of liquid and gas. Also, a void 252 is provided in top portion 222 to accommodate a holder for the photodetector, and a similar void 253 is provided in lower portion 220 to accommodate a holder for the photodiode. Similarly a conduit 260 through bottom portion 220 and conduit 261 through top portion 222 provide paths for the electrical leads from the diode and detector, respectively, to solder pads 230 and 231 which are located at the ends of electrical runs 233 and 234, and to the outside generally for the detector signal lead. Power is provided to the photodiode and the detector via input terminals 235 and 236. Terminals 237 and 238 provide a common ground for both the photodiode and the detector.

SYNTHESIZER OPERATION

Synthesis of a peptide is initiated by first loading the reaction vessel with resin, typically to which is attached the first amino acid in the sequence, and entering the desired amino acid sequence into the computer. The operator then loads the amino acid cartridges into the autodelivery system in the linear sequence or chain that corresponds to the amino acid sequence of the desired desired peptide.

A cycle of activation begins when needles 121 and 123 puncture the septum of the first cartridge, and needle 123 injects a calibrated amount of DCM. Gas sparges from needle 121 are used to mix and dissolve the protected amino acid in the DCM. After dissolution the protected amino acid is educted and transferred to the activator vessel. To assure total transfer of the protected amino acid, a second (and perhaps third) volume of DCM is added to the cartridge and then transferred to the activator vessel. Then, based on the amino acid, 0.5 equivalent of DCC in DCM is delivered to the activator vessel and the solution is mixed by periodic gas burps, e.g. argon or nitrogen. After a predetermined time interval sufficient for complete conversion of the amino acid to its symmetric anhydride, the gas line of valve block 25 is opened and the DCM solution of the PSA is pressured out through valve block 23 to the concentrator vessel. Frit 17 at the bottom of the activator vessel retains all of the DCU precipitate that is formed as a by-product in the activation reaction. With software control, the PSA reaction times can be individually adjusted for each amino acid to optimize PSA formation and for maximum precipitation of DCU. After transfer of the PSA/DCM solution to the concentrator vessel, a volume of DMF is added. The vent on the valve block 33 is then opened and an inert gas sparge through valve block 41 is commenced to volatilize the DCM. This is done without significantly reducing the original volume of DMF, which has a significantly higher boiling point than DCM. Heat is supplied by band heater 37 to replace heat lost by evaporation of the DCM. During this solvent replacement process, different maximum internal temperatures can be automatically adjusted to the unique thermal stabilities of the various protected amino acid PSA's by the use of thermistors. Concurrently with the solvent replacement process in the concentrator, the DCU precipitate in the activator is removed by successive washings with an alcohol/DCM mixture via (valve block 25) and overhead wash nozzle 19. The activator is finally washed with dichloromethane in preparation for the next PSA reaction. In the concentrator vessel after the dichloromethane has been removed, the PSA/DMF solution is pressure transferred from the concentrator vessel to the reaction vessel which contains the resin-bound alpha-amino-deprotected growing peptide chain.

The PSA/DMF that has been brought into the reaction vessel from the concentrator vessel reacts with the deprotected alpha-amino function of the resin bound peptide for a period of time sufficient for reaction completion (typically greater than 99%), after which spent reagent and solvent are washed out by successive solvent washes while using vortex agitation.

To begin a new cycle of synthesis in the reaction vessel it is first necessary to remove the alpha-amino protecting group of the last amino acid which was attached to the chain. In the specific case of t-BOC protected amino acids, a solution of trifluoroacetic acid (TFA) and DCM, typically 65% TFA, is pressure transferred to the reaction vessel and vortex agitation is periodically applied for effective mixing. After a time sufficient for total removal of the t-BOC-alpha-amino protecting groups (typically about 15 minutes), the fluid is pressured out through valve block 45 to waste. The resin is then washed rapidly with small volume increments of DCM introduced either through the valve block 43 or the valve block 45 while vortexing. Neutralization is effected by the introduction of diisopropylethylamine (DIEA) and DMF or DCM, vortexing, followed by pressure delivery to waste. Neutralization is usually repeated once. The resin is then washed by successive additions of DCM (or DMF) in small volume increments through valve block 45 with the top valve (valve block 43) open to waste, while vortexing (vortexing may be continuous or intermittent). After thorough washing of the amino deprotected resin, the next amino acid PSA/DMF mixture is pressure transferred to the reaction vessel from the concentrator vessel.

To sample the resin during synthesis or on completion of the peptide, first valve 55 is opened and line 61 is opened through valve block 45 which is vented to waste, while valve 67 is kept closed. The reaction vessel is then pressurized from the top while vortexing, forcing resin and the reaction solution into sample reservoir 57. This drives reasin against the membrane 59. Valve 55 is then closed, valve 67 is opened, and the waste line of valve block 45 is closed. DCM is passed back through line 61 from valve block 45 clearing resin from the membrane and depositing the resin/DCM mixture in a fraction collector 64. The sample reservoir and its accompanying tubing is then washed by closing valve 67, venting the reaction vessel, and transferring DCM through line 61 from valve block 45 through valve 55, and into the reaction vessel.

This integrated system allows for simultaneous operations in the reaction vessel and in the activator and concentrator vessels. For example, deprotection, neutralization, coupling, and washing operations can occur in the reaction vessel at the same time that the next amino acid PSA is being formed in the activator vessel. The concentrator vessel can be cleaned at the same time activation is occurring the activator vessel, and the activator vessel can be cleaned while the concentrator vessel is engaged in solvent replacement. This simultaneity of operations makes possible large economies in cycle time. Appendix A provides a more detailed description of this simultaneity by illustrating the time phasing of operations in each vessel during a complete process for attaching a single amino acid.

The system also allows the use of various synthesis methodologies. Although the approach described above has been for peptide synthesis by t-BOC-amino acid PSA's, alternative method using protected amino acid PSA's, such as F-MOC, could also be readily implemented. Similarly, synthesis could be implemented by using other active carboxyl species such as mixed anhydrides, active esters, acid chloride, and the like, utilizing the activator vessel and concentrator vessel to pre-form the activated carboxyl species just prior to introduction to the reaction vessel, thus eliminating the need for storage reservoirs of activated amino acid species which are maintained throughout the time frame of the peptide synthesis.

As indicated earlier special coupling procedures are necessary for asparagine, glutamine, and arginine and can be initiated in the activator and concentrator vessels. In these cases double couplings with hydroxybenzotriazole (HOBT) and DCC are generally required, where equimolar HOBT and DCC in DMF or DMF/DCM are pre-equilibrated and then combined with an equivalent of protected amino acid for reaction in the reaction vessel.

To achieve this result, one approach is to first transfer one equivalent each of HOBT/DMF and DCC/DCM to the concentrator vessel through valve blocks 23 and 41. Then two equivalents of protected amino acid from an amino acid cartridge are transferred to the activator vessel in appropriate solvents (DMF/DCM). Following that, half of the material in the activator vessel is transferred by time-pressure control to the concentrator vessel (containing the pre-equilibrated HOBT/DCC/DMF/DCM) for activation, after which the activated mixture is transferred to the reaction vessel. Analogous activation is commenced for the second coupling near the end of the first coupling cycle by recharging the concentrator vessel with a second equimolar mixture of HOBT/DCC, followed by addition of the second equivalent of amino acid from the activator vessel.

COMPUTER SOFTWARE SYSTEM

At the most basic level, software control of the apparatus is a matter of turning valves and other switched devices on and off at the proper times to achieve the desired flows of the various materials from one container or vessel to another. At the same time, many of the various steps in solid phase synthesis are quite repetitive and not extraordinary in number. Such a situation lends itself conveniently to a more sophisticated control concept aimed at functional control by the operator rather than having the operator dictate in detail the workings of individual valves to achieve a desired result. For example, most often the operator would rather command the system to transfer the contents of the activator vessel to the concentrator vessel, rather than formulate a more detailed series of commands such as: (1) check the concentrator vessel to see if it is ready to receive; (2) open the vent on valve block 33; (3) open valve blocks 23 and 41 at the connection of the transfer line between the vessels; (4) open gas valve to pressurize the activator vessel; (5) shut off the valves after a signal from liquid sensor 39 indicates that the fluid has been transferred. To achieve this kind of user-friendly approach and still maintain the capability of totally independent control over each element of the apparatus, the software control system is implemented through the touchscreen using a series of menus, which serve to provide the operator with a wide gamut of possibilities, from one extreme of using the system in a completely automated mode to the other extreme of operating the system by switching the individual valves.

The control concept involved is that each individual coupling of an amino acid to the peptide chain corresponds to three complete cycles: one cycle in the activator vessel, one cycle in the concentrator vessel, and one cycle in the reaction vessel. Each of these cycles consists of an ordered set of timed individual steps, each of which corresponds to a function which can occur in that vessel. As a general definition, a function can be considered as corresponding to a named set of switches which are turned on simultaneously (the normal position of each switch being off). In practice it is advantageous to number the varvious functions and to separate them by vessel. A function for example, might be DCM TO ACTIVATOR. Such a function requires a particular configuration of open valves in order for DCM to be delivered to the activator. In a cycle of the activator, this function may appear several times, e.g. after the bulk of symmetric anhydride has been transferred to the concentrator vessel it may be advantageous to wash the activator vessel and DCU precipitate several times with DCM to remove any residual symmetric anhydride. Each time this function occurs it will correspond to a different step in the reaction cycle occurring in the activator vessel, and similarly for other functions which are required in each cycle. The net result is that each cycle in a vessel is a series of steps, with each step corresponding to a function associated with that vessel. A typical list of functions is provided in Appendix B. To better illustrate this concept, the individual control menus will now be described.

Figure 8:
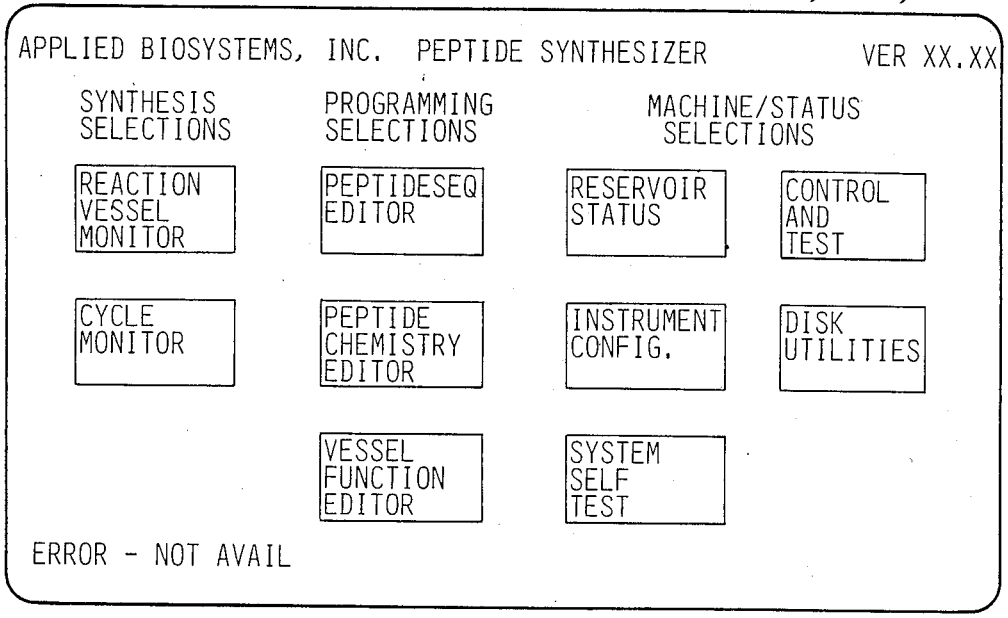
Figure 9:
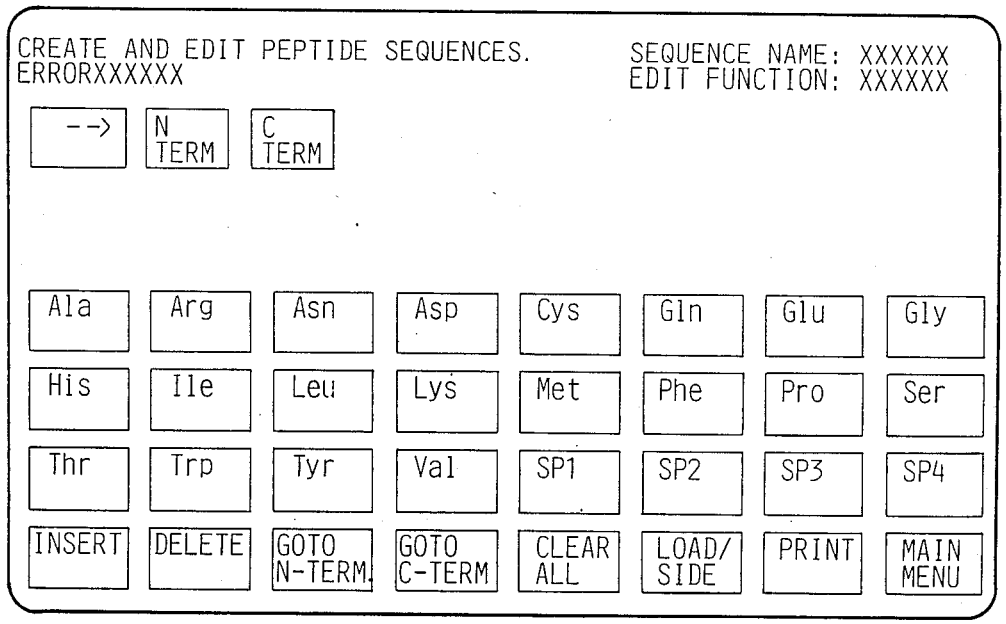
Figure 17A:
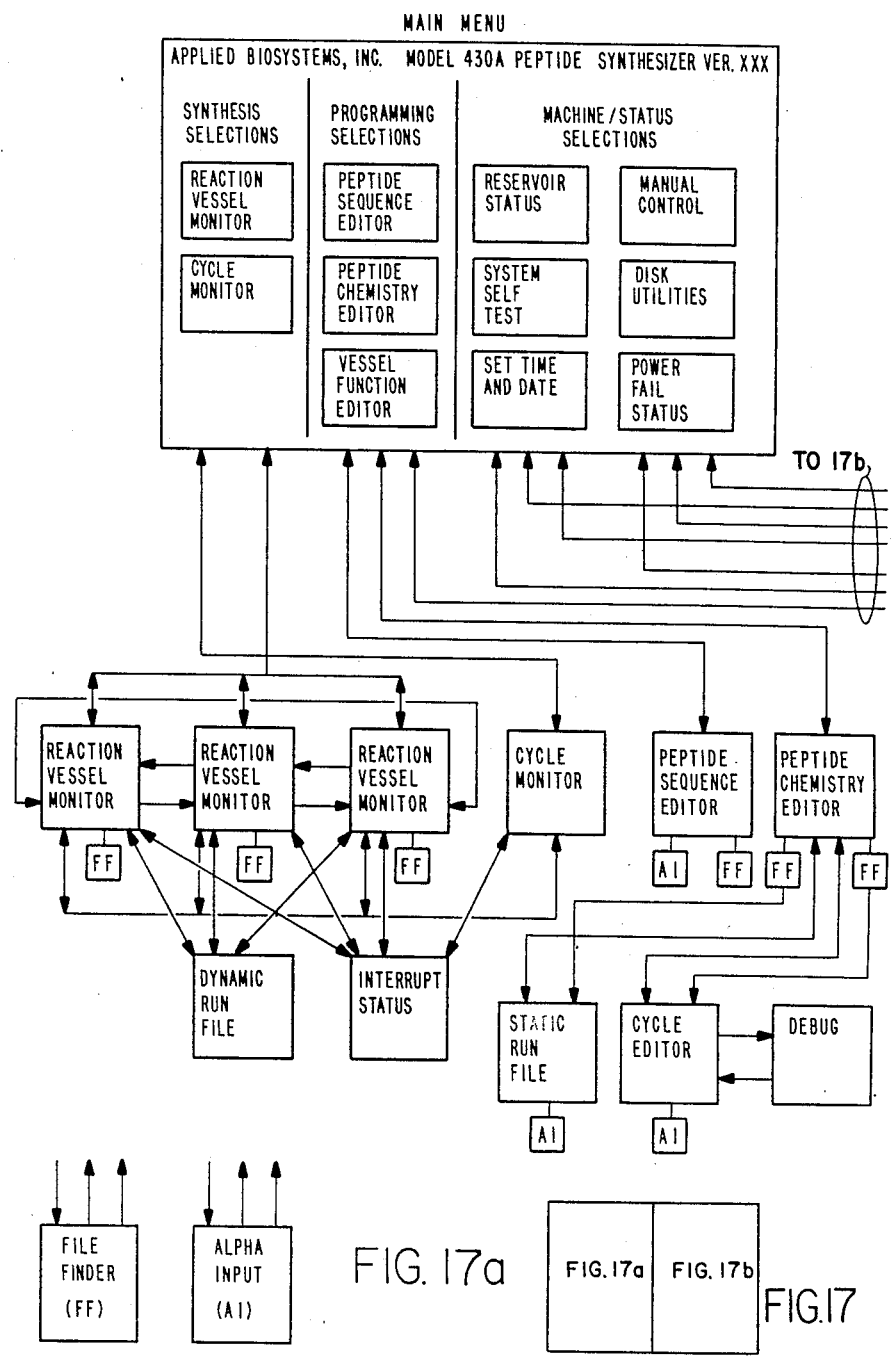
FIG. 17 is a menu flow scheme.
Figure 17B:
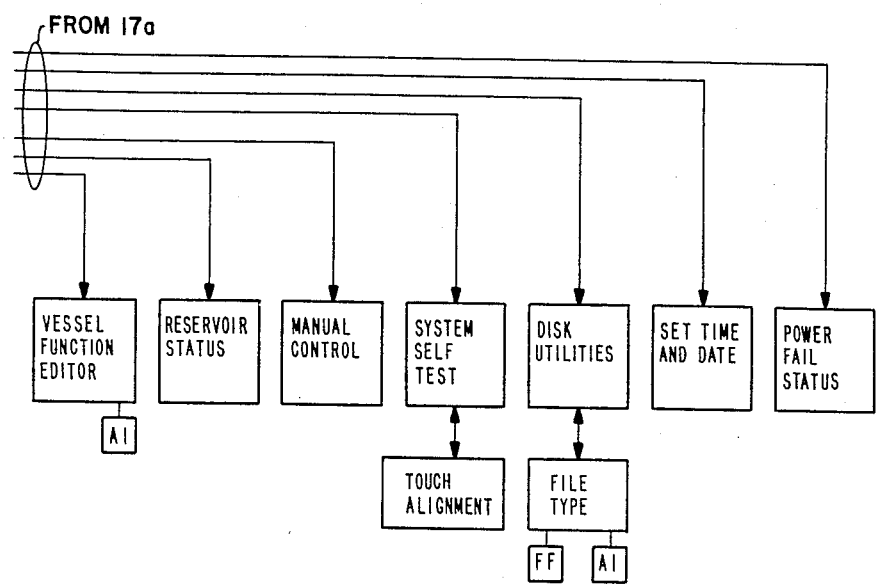

FIG. 8 shows the main menu of the system as it appears on the touchscreen, which corresponds to the bottom of a tree (shown in FIG. 17) of various other more detailed menus. Each outlined block corresponds to an area on the touchscreen by which the series of menus in that tree is accessed. For example, touching the screen at the block labeled "PEPTIDE SEQ. EDITOR", initiates another display, FIG. 9, listing all of the amino acids, and allows the selection and display of the order of amino acids from N to C terminus appearing in the peptide to be synthesized by simply touching the block containing the name of the desired amino acid in the desired sequence.

Figures 10, 11:
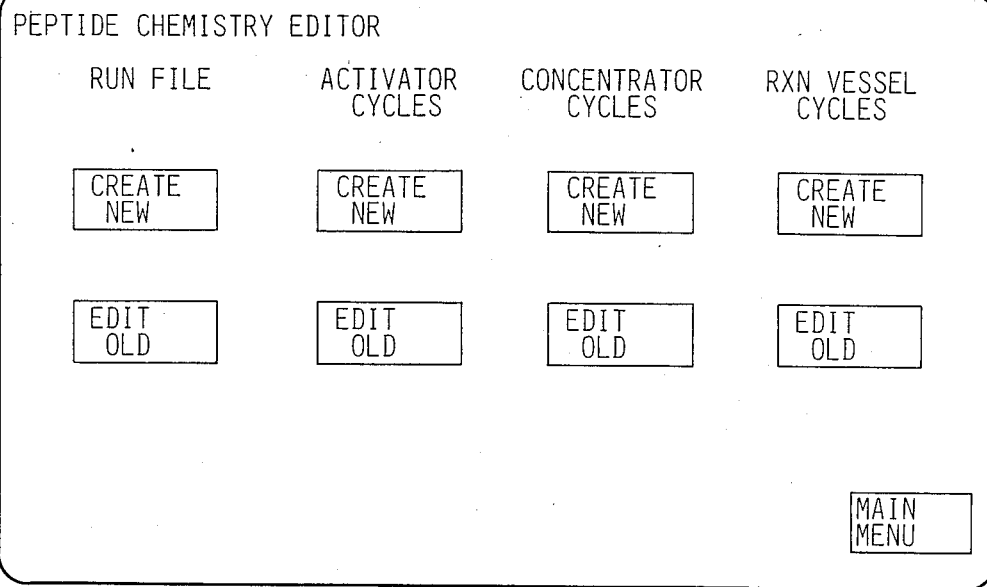

Touching the screen at the block labeled "PEPTIDE CHEMISTRY EDITOR", when the main menu is displayed brings up the PEPTIDE CHEMISTRY EDITOR menu, FIG. 10, which allows the operator to create or edit either cycle specifications in a particular vessel or the run file specification. As an example, if it is elected to create or edit a new activator cycle, a CYCLE EDITOR menu corresponding to the activator vessel appears on the screen. (See FIG. 11.) This menu enables the operator to change the order of the functions involved in each cycle of the activator, and similarly for menus corresponding to the other vessels.

Generally, a given cycle has three time fields associated with it: a required primary time, "TIME"; a time based on detector measurements, "MIN TIME" and "ERR MODE"; and an additional time added for particular sets of steps in the reaction vessel, "ADD TIME". TIME has several purposes. When liquid detection is not specified for the step, TIME is the total time for the step. When liquid detection is specified, the primary time is the "time out" or maximum time allowed before continuing regardless of whether or not the appropriate transition was detected by the liquid sensor. Also, when liquid detection is specified, the user must specify a minimum time, MIN TIME, before the appropriate transition (liquid to gas or gas to liquid) is to be registered. It is important to note another effect of TIME when detection is specified. When the sensor indicates the correct transition has occurred after the specified minimum time, the indicated function will be terminated, i.e., the switches for that function will be turned off. However, the next step will not be initiated until the primary time has elapsed. This is necessary to ensure proper alignment of the cycles in each vessel to obtain optimum throughput. ERR MODE is used in the event that detection is specified and the specified transition is not seen before the primary time has elapsed, e.g. if a valve is blocked or a particular reservoir is empty. This mode can be used to trigger an alarm or, in some cases, to effect a non-disastrous termination of the synthesis. ADD TIME refers specifically to the reaction vessel only, and corresponds to the amount of time (in tenths of a second) to be added to each of the three previous fields as a function of amino acid number in the sequence of the peptide being synthesized. Since the occupied volume in the reaction vessel increases with each additional amino acid coupling, the step times in the reaction vessel also increase. For example, if the value 10 is entered into this field, one second (10/10ths) will be added to the primary time for the second amino acid to be coupled in the peptide sequence. For the third amino acid, the time would be increased by two seconds, and so forth.

It it is desired to edit a RUN FILE, EDIT OLD in the PEPTIDE CHEMISTRY EDITOR is selected, displaying the RUN FILE EDITOR menu shown in FIG. 12. The table displayed therein corresponds to what is called the static run file. This file designates three cycles (one each for the activator vessel, the concentrator vessel, and the reaction vessel), for each of twenty six amino acid possibilities, and allows independent adjustment of the concentrator temperature for each amino acid. The twenty six amino acid possibilities provided are comprised of the twenty standard amino acids, an additional four for specialized use as might be desired by the operator, and a BEGIN cycle and an END cycle to allow independent control of these points in the synthesis. This static run file is the result of specifying the chemistry for each cycle through the various CYCLE EDITORS which have already been described). In addition, all cycles designated by a particular run file must be resident on a disc currently installed in the system, since the RUN FILE EDITOR will only allow choices from a list of resident cycles. Also, each of the three reaction vessels may synthesize from a different (or the same) run file, since, at the time a run is set up, the run file is specified for the particular vessel in the REACTION VESSEL MONITOR (which will be discussed later). Typically, the operator may create, edit, and store a number of run files on a single disc (up to 20). It should also be noted that although the system is designed to permit a different cycle for each amino acid possibility, it has been found in practice that not nearly that many cycles are needed to provide efficient operations.

The next menu which will be discussed in the VESSEL FUNCTION EDITOR. This menu is accessed from the main menu, and operates at the most basic level of the synthesizer. It involves the individual instructions required to accomplish a particular function in a particular vessel. For example, if it is desired to change the definition of a function or add or delete functions which are to occur in the activator vessel, the FUNCTION EDITOR shown in FIG. 13 corresponding to the activator vessel is called. Here, the entire set of functions for the activator can be reviewed and changed. As indicated earlier, a function is a named set of switches turned on simultaneously. These functions usually create a chemical flow path through the system. For example, the function "DCC TO ACTIVATOR" may be defined as switches 114 (DCC delivery valve in valve block 23), 116 (open DCC delivery valve), 119 (pressurize DCC bottle), and 125 (open activator to vent). Also some functions describe mechanical or electrical actions only, such as "heater on", (one switch). The system is organized into three types of functions: ON/OFF, TOGGLE ON, and TOGGLE OFF, specified as type 0, 1, and 2, respectively. An ON/OFF function turns switches on for a given step in a cycle only. At the end of that given step, all switches for that function are cleared (turned off) before the next function is activated. A TOGGLE ON function directs the machine to turn on certain switches and leave them on until a corresponding TOGGLE OFF function turns them off. Subsequent functions will not affect the state of the switches turned on by the TOGGLE ON function. Hence, during creation and editing of functions, it is important that all TOGGLE ON functions have a corresponding TOGGLE OFF function. Examples of TOGGLE ON functions are "Heater on" for the concentrator vessel, or "VORTEX ON" for the reaction vessel.

Calling the REACTION VESSEL MONITOR from the main menu presents the screen shown in FIG. 14, which lets the operator set up and monitor the synthesis. Two response fields permit the operator to select between two modes of operation, a first mode which automatically controls the apparatus based on the input to the PEPTIDE SEQ. EDITOR and a set of preprogrammed cycles called the dynamic run file; and a second mode which operates based only on which cartridges (kinds of amino acids) are loaded into the autodelivery system and a set of preprogrammed cycles from a designated static run file. If the first mode is chosen, the computer initiates a question as to whether the operator wishes to change the dynamic run file. If so, the operator responds in the affirmative and a screen as shown in FIG. 15 is displayed, corresponding to an editor for the dynamic run file. This file is generated initially internally when the operator enters the desired peptide sequence into the PEPTIDE SEQ. EDITOR. It is simply a table listing the sequence of amino acids in the order to be synthesized, with the designated cycles for each amino acid as has already been programmed from the designated static run file. This editor is designed so that the operator can alter the cycles used for particular amino acids in the sequence depending on where they are located in the peptide chain, so that the operator has position dependent control over the chemistry. Unlike the static run file, the dynamic run file is not stored on the disc.

Following mode selection in the REACTION VESSEL MONITOR, a series of questions is then generated to ensure that the apparatus is properly set up to begin operations, e.g. checks are made as to whether the reaction vessel is loaded, and whether the autoloader has the desired number and order of amino acids.

Following that series of inquiries, the final inquiry is whether to begin or to stop operations. Also as part of the function of the REACTION VESSEL MONITOR, the status of the reaction vessel is displayed, including the name of the activated amino acid that is currently undergoing reaction, the time that the synthesis of peptide was initiated, and the time when the synthesis was completed. In addition, the current coupling is displayed and the sequence of couplings already completed can be displayed and reviewed by scrolling back and forth on the screen.

Calling the CYCLE MONITOR from the main menu brings up the screen shown in FIG. 16. Here the current status of each vessel is displayed in real time in terms of several parameters. On the first line is listed for each vessel the particular number of the amino acid in the sequence of the peptide which is currently active in that vessel, along with the abbreviation of the name of the particular amino acid. The second line lists the particular cycle name currently ongoing in each vessel. The third line lists which step in the sequence of steps of the particular cycle is currently being carried on in each vessel. The fourth line lists the number of the function and the function name corresponding to the particular step listed for that vessel. Also the elapsed time into each cycle is listed as is the status of each of the liquid sensors.

Several other menus may also be selected from the main menu under the general category of MACHINE/STATUS SELECTIONS. These include: RESERVOIR STATUS which relates to the fact that the apparatus monitors the volume used from each reservoir during each cycle, so that when a reservoir runs low an alarm is registered to inform the operator of the problem; INSTRUMENT CONFIG. which is used to display and set the configuration of the machine itself, e.g. time of day, power line —120 V at 60 Hz, etc.; SYSTEM SELF TEST which tests all of the electronic functions to the extent practicable; CONTROL AND TEST which allows manual control of the apparatus to the extent that the operator can manipulate each valve and switch, one at a time, in order to facilitate debugging and to enable manual intervention of synthesis if necessary; and DISK UTILITIES which allows the operator to carry out customary disc functions necessary to the operation of a computer system, e.g. setting up files, purging files, and renaming files.

Another characteristic of the apparatus which is controlled by the software is the simultaneity of operations in the reaction vessel, the concentrator vessel, and the activator vessel. By noting the various times required to carry out each step of a cycle in each vessel, an automated optimization scheme, hereinafter called a cycle compiler, has been developed to provide maximum efficiency in the synthesis of each particular peptide given a particular chemistry. To achieve this efficiency it is important to recognize that for each vessel certain events (functions) in time, in each cycle, determine when transfers can take place and when the vessel is ready to being the process for another transfer. For the activator vessel, these functions correspond to the beginning of a transfer, BOTA; the end of a transfer, EOTA.

Similarly for the concentrator cycle, the key functions include identifying when the vessel is ready to receive, RC; as well as the beginning of a transfer, BOTC; the end of a transfer, EOTC. For the reaction vessel, these functions delineate when the vessel is ready to receive, RR. Using these concepts, a graphic representation of a cycle as it takes place in each vessel can be depicted as illustrated in FIG. 18. From this figure, it is apparent that one of the first criteria for operation is that $$T_{BOTA}=T_{RC} \text{ and } T_{BOTC}=T_{RR};$$

i.e. the concentrator vessel must be ready to receive when a transfer from the activator vessel is begun, and the reaction vessel must be ready to receive when a transfer from the concentrator vessel is begun. The next step then is to determine in which vessel operations should begin first, in order to optimize the process. This can be accomplished by calculating the left side delays (from FIG. 18) for each vessel: $T_{DLA}$, $T_{DLC}$, and $T_{DLR}$. These left side delays pertain to the waiting time allowed before preparing the particular vessel for the function that is to take place there, e.g. for the activator vessel, some waiting time may be allowed before transferring amino acid into the vessel and creating the symmetric anhydride, and for the reaction vessel, there may be some waiting time allowed before beginning the deprotection of the resin bound peptide chain. Once these left side delays are calculated, the shortest delay (i.e. the longest preparation time) then corresponds to the cycle which should begin first, and the master time should be equal to zero for that cycle. These various delays can be calculated according to the following equations. First define $$T_{MA} \equiv (T_{EOTA} - T_{BOTA}) + (T_{BOTC} - T_{RC}), \text{ and}$$

$$T_{ML} \equiv MAX(T_{BOTA}, T_{RC}, T_{RX}),$$

where $$T_{RX} \equiv T_{RR} - T_{MA}. \text{ (See FIG. 18 for a physical interpretation of } T_{MA} \text{ and } T_{ML}\text{)}$$

Then $$T_{DLA} = T_{ML} - T_{BOTA},$$

$$T_{DLC} = T_{ML} - T_{RC}, \text{ and}$$

$$T_{DLR} = T_{ML} - T_{RX}.$$

For example, setting the master time equal to zero at the beginning of the cycle shown in FIG. 18 might yield delay times such as $T_{DLA}=0$, $T_{DLC}=5$, and $T_{DLR}=3$, i.e. the activator vessel would begin first at time $T=0$ the reaction vessel then would begin 3 seconds later, and the concentrator vessel would begin at $T=5$ seconds.

The next requirement for optimal throughput involves calculating the minimum separation of these three cycles with the three cycles of the next coupling sequence. To calculate this minimum, it is important to evaluate the right side delays for the first cycle:

$$T_{DRA} = T_{BOX} - T_{DLA} - T_{AT},$$

$$T_{DRC} = T_{BOX} - T_{DLC} - [T_{CT} + (T_{EOTA} - T_{BOTA})];$$

and $$T_{DRR} = T_{BOX} - T_{DLR} - [T_{RT} + (T_{EOTC} - T_{BOTC})];$$

where $$T_{BOX} = MAX[(T_{AT} + T_{DLA}),$$

$$(T_{CT} + (T_{EOTA} - T_{BOX}) + T_{DLC}),$$

$$(T_{RT} + (T_{EOTC} - T_{BOTC}) + T_{DLR})];$$

and where $T_{AT}$, $T_{CA}$, and $T_{RT}$ correspond to the total time for the activator cycle, concentrator cycle, and reaction vessel cycle, respectively.

These right side delays must then be combined with the various left side delays for the next cycle to arrive at a minimum separation for the three cycles, i.e.

$$T_{Sc2-c1} = MIN[(T_{dra} + T_{DLA2}), (T_{DRC} + T_{DLC2}), (T_{DRR} + T_{DLR2})],$$

where $T_{Sc2-c1}$ is the minimum separation between the first cycle and the second cycle, and $T_{DLA2}$, $T_{DLC2}$, and $T_{DLR2}$ are the left side delays of the second cycle (calculated using the same technique as for the left side delays in the first cycle).

Figure 19:
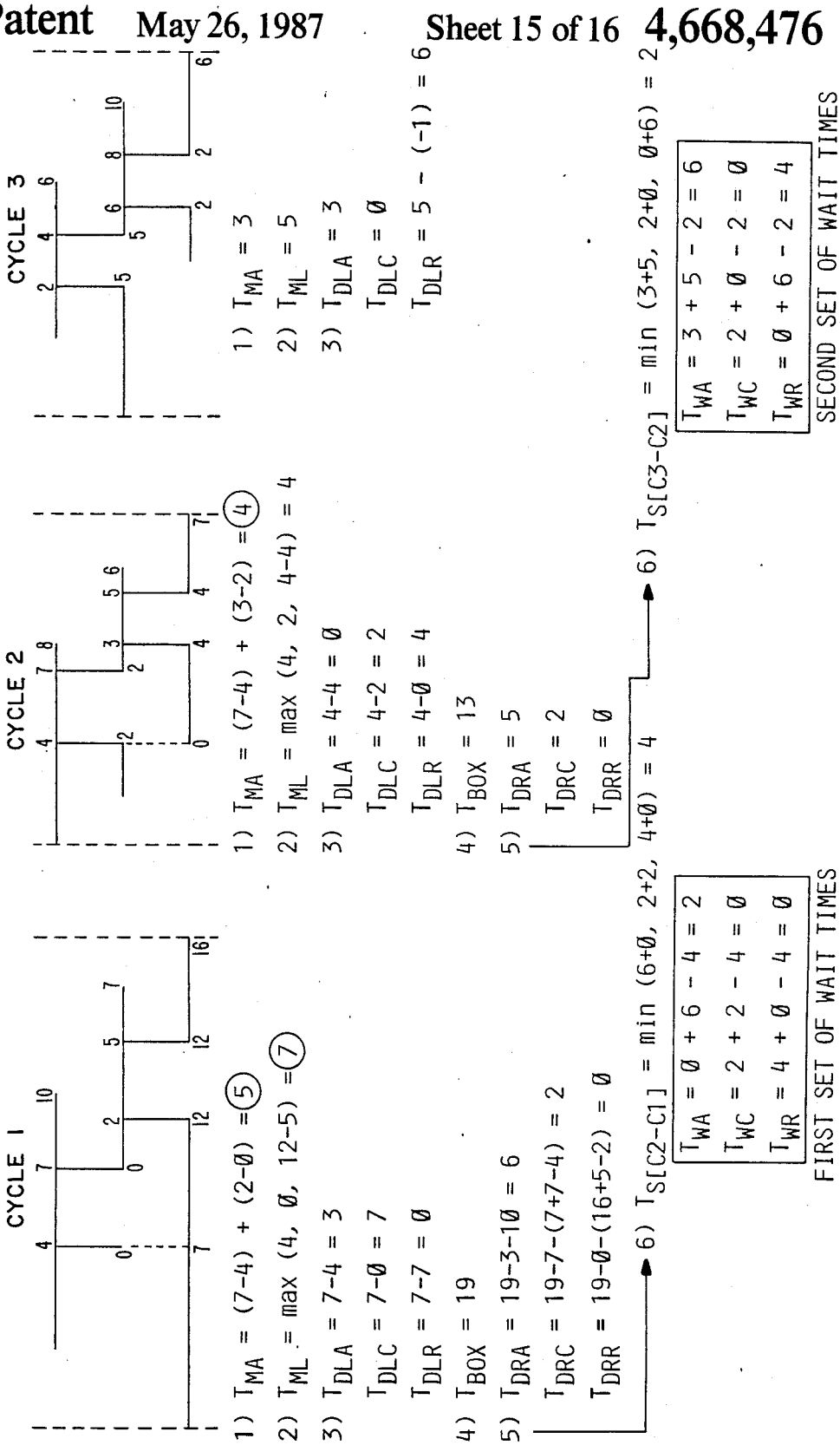
FIG. 19 provides an example of a calculation for optimizing the production of a peptide which requires three cycles of coupling.

This minimum separation can then be translated into the waiting times required to start the second cycle in each of the vessels, i.e.

$$T_{WA2} = T_{DLA2} + T_{DRA} - T_{Sc2-c1},$$

$$T_{WC2} = T_{DLC2} + T_{DRC} - T_{Sc2-c1},$$

and $$T_{WR2} = T_{DLR2} + T_{DRR} - T_{Sc2-c1}$$

where $T_{WA2}$, $T_{WC2}$, and $T_{WR2}$ are the waiting times for the activator vessel, the concentrator vessel, and the reaction vessel, respectively, from the last step of the first cycle to the first step of the second cycle. In order to achieve optimum efficiency one of $T_{WA2}$, $T_{WC2}$, and $T_{WR2}$ must be zero, as was the case for left side delays in the first cycle. FIG. 19 shows the results of the above calculation for a series of three cycles.

UTILITY OF THE INVENTION

The ability to deliver amino acid symmetric anhydrides of predetermined integrity to the reaction vessel enables most coupling reactions to proceed in yields exceeding 99% using just single couplings. Because of this very high yield at each step, it is possible to synthesize peptides with very high overall efficiency fully automatically. The combination of activator vessel and thermally jacketed concentrator vessel make it possible to study and develop optimal conditions for maximal symmetric anhydride formation for individual protected amino acids, by individually modifying stoichiometry, reaction times in DCM, temperature during DMF replacement of DCM, and the time frame during which the solvent replacement process is executed. Thus, for each type of amino acid it is possible to automatically implement conditions which will reproducibly deliver a maximal quantity of symmetric anhydride to the reaction vessel containing the peptide resin.

In the prior art with peptide synthesizers having no ability to form preactivated amino acids, the user is obliged to stop at each reaction cycle after coupling to monitor the extent of coupling. Then with the objective of improving the yield, second, or even third couplings can be effected in cases where the first coupling reaction was relatively inefficient. The result is automation of a single cycle of synthesis at the preclusion of automation from cycle to cycle. Alternatively, existing synthesizers can be used automatically from cycle to cycle by utilizing multiple couplings with in situ activation in the reaction vessel containing the peptide resin. This results in relatively inefficient couplings since the activation method cannot be uniquely optimized for individual amino acids in the presence of the reacting amino group of the growing peptide chain.

Figure 20A:
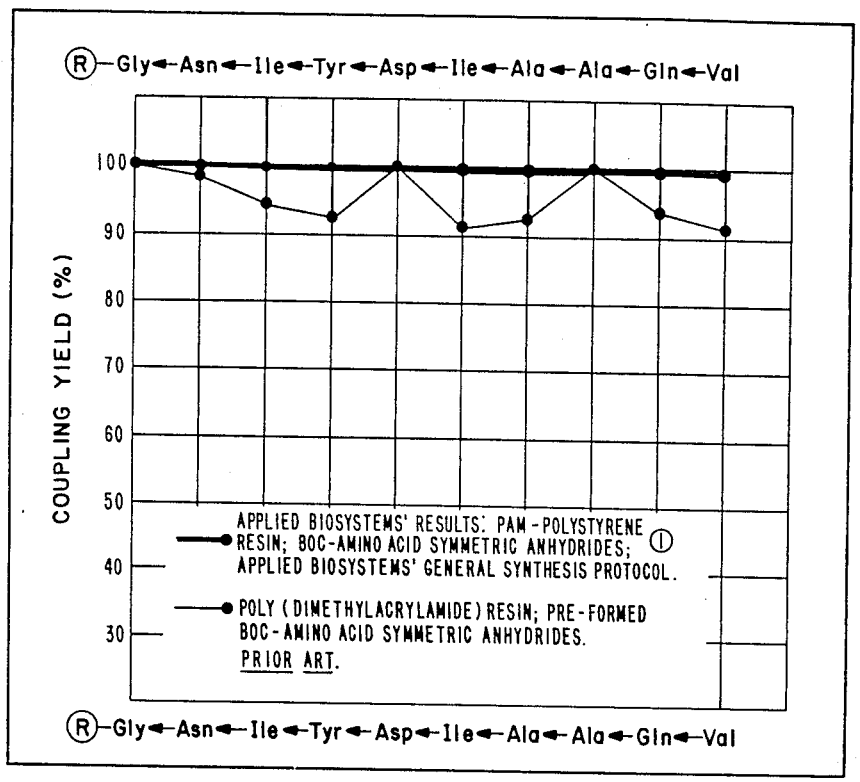
FIG. 20 shows a comparison of the prior art with the apparatus of the invention with regard to synthesized peptide purity.

The results shown in FIG. 20 illustrate the relative advantage of the claimed apparatus for the synthesis of the decapeptide Acyl Carrier Protein (65-74). The uppermost line is a graphical representation of the individual cycle yields for each amino acid addition during the peptide chain assembly as performed on the apparatus of the invention. Except for glutamine (symbolized by Gln), all amino acid additions were accomplished by a fully automated sequence of single couplings: glutamine requires a special chemical protocol well known in the art that consists of double coupling with HOBT (hydroxybenzotriazole) activation. All other couplings were done with Boc-amino acid symmetric anhydrides.

The lower line depicts results of the synthesis of the same peptide on a Beckman 990 Peptide Synthesizer using Boc-amino acid symmetric anhydrides preformed manually, off the instrument. Reference: Reza Arshady, Eric Atherton, Derek Clive, and Robert C. Sheppard *J. Chem. Soc. Perkin Trans* 1, (1981) 529-537. The results demonstrate that fully automated synthesis was precluded by the need to manually preform the symmetric anhydrides, and that the manually preformed symmetric anhydrides were not optimally formed.

Some peptide amino acid sequences demonstrate unique, sequence specific coupling problems where even second and third couplings, typically in DCM, fail to effect greater than 99% coupling yields, irrespective of the activated form of the amino acid (see W. S. Hancock, D. J. Prescott, P. R. Vagelos, and G. R. Marshall, *J. Org.* 38 (1973) 774). However, those skilled in the art recognize that sequence dependent incomplete couplings performed in poor solvents such as DCM would be much improved if performed exclusively in more polar solvents such as DMF (see S. Meister, S. B. H. Kent, *Peptides, Structure & Function, Proceedings of the 8th American Peptide Symposium*, pps. (103–106). The Acyl Carrier Protein (65–74) decapeptide is such a known problem sequence and the excellent results achieved on the claimed apparatus by coupling with Boc-amino acid symmetric anhydrides in DMF demonstrate one of the chief advantages of the apparatus: optimal formation of the activated amino acid in DCM, but coupling of the activated amino acid in DMF. This automatically executed method affords a general solution to the synthesis of problem peptide sequences.

APPENDIX A

Example of a typical Amino Acid Pre-formed
Symmetric Anhydride Cycle
For all amino acids except GLN, ASN and ARG.
Each line described is a separate type of function.
A function opens specific valves for a given operation.
DCM = Dichloromethane; DMF = N,N—Dimethylformamide;
DCC = N,N—Dicyclohexylcarbodiimide; TFA = Trifluoroacetic acid;
DIEA = Diisopropylethylamine

| Rx Vessel | Concentrator | Activator |
|---|---|---|
|  |  | Advance Fraction collector (for Resin collector) |
|  |  | Needle down |
|  |  | DCM to cartridge |
|  |  | Mix cartridge |
| If this is the first cycle of a series then the resin is washed 3 times with DCM (all washes include vortexing)* |  | Wait to dissolve amino acid |
|  |  | Transfer Amino Acid to Activator rinse cartridge (DCM) ⎫ |
|  |  | ⎬ repeat once |
|  |  | Transfer rinse to Activator ⎭ |
|  |  | Rinse cartridge ⎫ |
|  |  | ⎬ |
|  |  | Rinse to Waste ⎭ |
|  |  | Measure DCC |
|  |  | DCC to Activator |
|  |  | Reaction time in Activator of about |
| Add DCM to RV (~1.5 ml) |  | 10 min. (depending on amino acid)** - |
| Add TFA to RV (~3 ml) |  | series of waits & mixing during this |
| (This makes about a 65% dilution of TFA in RV) |  | time - if mixing does not occur at about 30 second intervals, then the precipitate forms a plug that will |
| Drain RV |  | not break up). This reaction is |
| Repeat above additions. |  | faster in DCM than DMF. |
| 65% TFA is then left in RV for ~15 min with mixing - for deprotection |  |  |
|  | Transfer contents of Activator |  |
| Rinse valve block 4 times to eliminate TFA - blow back gas into TFA bottle so that TFA is not sitting in line against valve block - | to concentrator | Rinse activator & precipitate with DCM from top of Activator twice & transfer each rinse to concentrator. |
| Vent TFA bottle so its not under pressure. | Blow nitrogen gas through contents. This cools the mixture rapidly. Heat the concentrator vessel | A combination of DCM and methanol are then added to yield approximately a 6/4 ratio to dissolve the |
| During the 15 min. TFA time the resin sample line is rinsed with DCM twice. | so that the temperature doesn't exceed a certain point (depending on amino acid). | Dicyclohexylurea (precipitate). This dissolving takes a few minutes with mixing in between. |
|  | At various time intervals add DMF to the concentrator (~1 ml at a time, so that the DCM is effectively | Drain activator to waste. |
| At the end of 15 min. the RV is drained. | being replaced with DMF. This process will take from 5-15 min.*** | Rinse activator from top with DCM to eliminate the methanol. This is done in a series of rinses & drains with mixing in between. |
| Add DCM for fast wash ⎫ |  |  |
| ⎬ 3 times |  |  |
| Drain. ⎭ |  | The activator then waits for the |
| Add DMF (9 mls) ⎫ |  | next cycle |
| ⎬ 10% concentration |  |  |
| Add DIEA (1 ml) ⎭ |  |  |

APPENDIX A-continued

Example of a typical Amino Acid Pre-formed
Symmetric Anhydride Cycle
For all amino acids except GLN, ASN and ARG.
Each line described is a separate type of function.
A function opens specific valves for a given operation.
DCM = Dichloromethane; DMF = N,N—Dimethylformamide;
DCC = N,N—Dicyclohexylcarbodiimide; TFA = Trifluoroacetic acid;
DIEA = Diisopropylethylamine

| Rx Vessel | Concentrator | Activator |
|---|---|---|
| Mix with top vent open so that top line is washed (TFA is neutralized) <br> Add DIEA & DMF to the resin sample line (to neutralize any TFA that may have entered the line). <br><br> Drain RV <br> Repeat DIEA, DMF <br> Drain RV <br> Add DMF } repeat 6 times <br> Drain <br><br> Also rinse resin sampler line during this time with DMF | | |
| Transfer content of concentrator (~4-ml) to RV <br><br> Reaction time of 30 min. <br><br> (Rinse resin sampler line during this time periodically.) <br><br> At end of Rx time, drain RV <br> Wash with DCM } 6 times <br> drain <br> Before last drain of RV - remove resin sample from RV and transfer to fraction collector | Rinse concentrator with DMF from top (twice) & transfer each wash to RV <br><br> Wash concentrator thoroughly with DCM - series of washes from top and drain. <br><br> Wait for next cycle. | |

NOTES:
Washes of RV are 10 ml each. Start vortexing at beginning of addition of wash solvent. This helps to break up any resin agglomeration. Option: washing from top or bottom of RV.
Valve blocks are washed with DCM and blown out with nitrogen after transfers and deliveries of certain reagents.
*The resin used is typically loaded PAM-Resin (1% styrene Divinyl benzene resin). The carboxy terminal amino acid is loaded onto the resin through an organic linker. Typically, 0.5 m moles of loaded resin (~1 m mole amino acid/gram polystyrene) is used.
**10 min. is used for all amino-acids except GLN, ASN, and ARG. However, individual variations can be incorporated at the request of the operator.
***For Tyrosine and Lysine approximately 7 min. is typical; and for all others, except GLN, ASN and ARG, 15 min. is typical.

APPENDIX B

LIST OF POSSIBLE FUNCTIONS FOR PEPTIDE SYNTHESIZER
Key: T = top valve block; B = bottom valve block; 0 = off; 1 = on Reaction Vessel Functions
DCM to waste (T)
Extra to waste (T)
gas VB (T)
Vent RV (T)
Pressurize RV (T)
DCM to RV (T)
DCM to waste (B)
DMF to waste (B)
DIEA to waste (B)
DIEA Pressure
TFA to waste (B)
gas VB (B)
Drain RV (B)
Blow back into TFA bottle
Vent TFA bottle
TFA Pressure
Manifold Pressure
Neutralizer Pressure
Neutralizer Delivery
Vent RV (B)
Pressurize RV (B)
DCM to RV (B)
DMF to RV (B)
DIEA to RV (B)
TFA to RV (B)
Gas to RV(B)

Resin Sampler (RV functions)
take sample
DCM to RV
DCM to fraction collector
DMF to RV
DMF to fraction collector
Gas to RV
Gas to fraction collector
DIEA to RV Misc RV Functions
Vortex (0,1)
Fraction collector advance
Concentrator

APPENDIX B -continued

DMF to waste (T)
DCM to waste (T)
Gas VB (T)
Pressurize Conc (T)
Vent (T)
Drain
DCM to Conc (T)
DMF to Conc (T)
DMF to waste (B)
Extra to waste (B)
Gas VB (B)
Pressurize Conc (B)
Vent (B)
DMF to Conc (B)
Extra to Conc (B)
Manifold Pressure

*Transfers*

Conc to RV
DMF transfer line
Extra to transfer line
Gas transfer line

*Misc Conc Function*

Heater (0,1)

*Activator*

MeOH to waste (T)
DCM to waste (T)
Gas VB (T)
Pressurize Act (T)
Drain Act
Vent Act (T)
DCM to Act (T)
MeOH to Act (T)
DCM to waste (B)
Extra-1 to waste (B)
DMF to waste (B)
Extra-2 to waste (B)
AA to waste (B)
Gas VB (B)
Measure DCC
Measure HOBT
Manifold Pressure
Pressurize Act (B)
Gas to mix (B)
DCM to Act (B)
DMF to Act
DCC to Act
HOBT to Act
Amino Acid to Act
Extra-1 to Act
Extra-2 to Act

*Cartridge Delivery System*

DCM to cartridge
DMF to cartridge
Extra-1 to cartridge
Extra-2 to cartridge
Pressurize cartridge (sample needle)
Pressurize cartridge (vent needle)
Mix cartridge
Vent cartridge (sample needle)
Vent cartridge (vent needle)

*Transfers*

Act to Conc
DCM transfer line
DMF transfer line
Extra-1 transfer line
Extra-2 transfer line
Gas transfer line

*Misc Act Functions*

Needle up & down (0,1)
Cartridge Eject

What is claimed is:

1. An automated peptide synthesizer comprising:
activation means for receiving protected amino acids, said activation means including a activation vessel in which to activate each of the amino acids;
reaction vessel means containing a support used in solid-phase peptide synthesis for attaching a peptide chain to said support;
transfer means connected to said activation means and to said reaction vessel means for transferring and mixing materials used in said synthesizer; and
computer means connected to said transfer means for automatically controlling said transfer means to cause a transfer of a sequence of aliquots of a preselected arbitrary sequence of amino acids into said activation means, one kind of amino acid at a time, for causing said transfer means to transfer a corresponding aliquot of an activating medium into said activation means for each of the aliquots of amino acid transferred into said activation means, for causing said transfer means to mix each of the aliquots in said sequence of aliquots of amino acids with its corresponding aliquot of activating medium to form a sequence of aliquots of activated species of amino acids corresponding to said preselected arbitrary sequence of amino acids, and for causing said transfer means to transfer each aliquot of the activated species of amino acid from said activation means into said reaction vessel means so as to introduce to said support a sequence of aliquots of activated species of amino acids, one kind of amino acid at a time.

2. A synthesizer as in claim 1 wherein said transfer means includes means for transferring a deprotection medium into said reaction vessel means, said transfer of the deprotection medium being controlled by said computer means to occur for each aliquot of the activated species which is followed by another aliquot of amino acid in said sequence of aliquots of amino acids.

3. A synthesizer as in claim 1 wherein said reaction vessel means includes agitation means for preventing agglomeration of said support during reaction with each of the activated species of amino acid.

4. A synthesizer as in claim 3 wherein said agitation means further comprises vortexing means for moving materials contained in said reaction vessel means by vortex action.

5. A synthesizer as in claim 4 wherein said reaction vessel means includes a container having an axis of rotational symmetry.

6. A synthesizer as in claim 5 wherein said agitation means comprises rotation means for causing one end of said container to execute a circular motion about said axis of rotational symmetry while the other end is held stationary.

7. A synthesizer as in claim 1 wherein said computer means comprises means for causing said transfer means to transfer the activating medium into said activator vessel to create each of the activated species of amino acid a short period of time before being transferred into said reaction vessel.

8. A synthesizer as in claim 7 wherein said activation means further comprises a concentrator vessel coupled to said activator vessel via said transfer means and coupled to said reaction vessel via said transfer means, and wherein said computer means further comprises means for causing said transfer means to transfer the activator solvent and each of the aliquots of the activated species of amino acid, one kind of amino acid at a time, from said activator vessel to said concentrator vessel for concentrating each of the aliquots of activated species of amino acid relative to the activator solvent.

9. A synthesizer as in claim 8 wherein said computer means further comprises means for causing said transfer means to remove the activator solvent from said concentrator vessel and to transfer a coupling medium into said concentrator vessel with each aliquot of the activated species of amino acids.

10. A synthesizer as in claim 9 further comprising heating means for heating said concentrator vessel, said computer means coupled to said heating means for controlling said heating means according to the kind of activated species of amino acid contained in said concentrator vessel.

11. A synthesizer as in claim 1 wherein said transfer means further comprises autodelivery means coupled to said computer means and controlled thereby for automatically supplying the amino acids, one kind at a time, to said activation means, in the order desired in the peptide, said autodelivery means having guideway means for holding individual containers of amino acid in a linear array in the order desired in the peptide, said guideway means configured so that the individual containers of amino acid can be moved along said guideway means.

12. A synthesizer as in claim 11 wherein said autodelivery means further comprises extraction means for extracting the contents of the individual containers, one container at a time.

13. A synthesizer as in claim 12 wherein said extraction means further comprises needle means configured for supplying solvent into a single one of the containers, for mixing the solvent and amino acid in the single one of the containers, and for extracting the solvent together with the amino acid from the single one of the containers.

14. A synthesizer as in claim 13 wherein said autodelivery means further comprises transport means for moving the containers along said guideway means and for positioning the containers, one at a time, proximately to said needle means.

15. A synthesizer as in claim 11 further comprising a linear array of individual containers held in said guideway means.

16. A synthesizer as in claim 15 wherein each of said containers has a bottom which internally has the shape of a trough.

17. A synthesizer as in claim 16 wherein said bottom of each of said containers is constructed to stand upright on said guideway means without external constraints.

18. A device for synthesizing a polypeptide comprising:
an activator vessel for receiving an amino acid, an activating reagent, and an activating solvent for creating an activated species of the amino acid;
filter means located in said activator vessel for filtering out a precipitate when removing the activated species and the activating solvent from said activator vessel, said precipitate formed when creating the activated species;
a concentrator vessel having concentrator vessel inlet means for receiving the activated species of the amino acid and the activating solvent, and for receiving a coupling solvent, said concentrator vessel having outlet means for venting said concentrator vessel to remove the activator solvent thereby concentrating the amino acid relative to the activating solvent;
a reaction vessel containing a support for solid-phase peptide synthesis on which to couple said reaction vessel having reaction vessel inlet means for receiving the activated species of the amino acid and the coupling solvent;
transfer means coupled to said activator vessel, to said concentrator vessel and to said reaction vessel for removing the activated species and the activating solvent from said activator vessel and for transferring the activated species and the activator solvent to said concentrator vessel, for exchanging the activator solvent with the coupling solvent in said concentrator vessel, and for transferring the activated species of amino acid and the coupling solvent from said concentrator vessel to said reaction vessel.

19. A device as in claim 18 wherein said concentrator vessel includes heating means for heating material contained in said concentrator vessel.

20. A device as in claim 19 further comprising computer means coupled to said heating means and to said transfer means, for controlling transfers by said transfer means according to a pre-programmed schedule, and for controlling heating by said heating means according to a pre-programmed schedule.

21. A device as in claim 20 wherein said transfer means includes a first tube connected between said activator vessel and said concentrator vessel and a first valve block means connected to and controlled by said computer means for controlling flow from said activator vessel to said first tube, and a second valve block means connected to and controlled by said computer means for controlling flow into said concentrator vessel from said first tube.

22. A device as in claim 21 wherein said transfer means also includes a second tube connected between said concentrator vessel and said reaction vessel and a third valve block means connected to and controlled by said computer means for controlling flow into said reaction vessel, and wherein said second valve block means also controls flow from said concentrator vessel into said second tube.

23. A device as in claim 22 further comprising resin sampler means coupled to said computer means and controlled thereby for extracting materials from said reaction vessel.

24. A device as in claim 22 further comprising liquid sensor means coupled to said computer means for detecting transitions between gases and liquid flowing in said first tube.

25. A device as in claim 20 wherein said computer means includes menu means categorizing physical and chemical operations in said device, for permitting control over said operations by an operator.

26. A device as in claim 25 wherein said menu means comprises a set of cycles, each cycle characteristic of a complete set of operations in one of said activator vessels, said concentrator vessel, and said reaction vessel.

27. A device as in claim 26 wherein said computer means includes memory means for storing an algorithm for calculating operating times of said first, second and third valve block means to maximize the production rate of a polypeptide given any particular sequence of cycles in each of said activator vessel, said concentrator vessel, and said reaction vessel.

28. A device as in claim 27 wherein said computer means includes means for calculating said operating times and switch means for operating said first, second, and third valve block means in accordance with said operating times.

* * * * *